(12) United States Patent
Landau et al.

(10) Patent No.: US 7,156,823 B2
(45) Date of Patent: Jan. 2, 2007

(54) HIGH WORKLOAD NEEDLE-FREE INJECTION SYSTEM

(75) Inventors: Sergio Landau, Laguna Niguel, CA (US); Daniel E. Williamson, Sherwood, OR (US)

(73) Assignee: Bioject Inc., Tualatin, OR (US)

( * ) Notice: Subject to any disclaimer, the term of this patent is extended or adjusted under 35 U.S.C. 154(b) by 0 days.

(21) Appl. No.: 10/458,345

(22) Filed: Jun. 9, 2003

(65) Prior Publication Data

US 2004/0111054 A1 Jun. 10, 2004

Related U.S. Application Data

(63) Continuation-in-part of application No. 10/164,920, filed on Jun. 4, 2002, now Pat. No. 6,676,630.

(51) Int. Cl.
*A61M 5/30* (2006.01)
*A61M 5/00* (2006.01)

(52) U.S. Cl. .................... 604/70; 604/110

(58) Field of Classification Search ........... 604/68–72, 604/187, 110
See application file for complete search history.

(56) References Cited

U.S. PATENT DOCUMENTS

| | | | |
|---|---|---|---|
| 2,653,604 A | 9/1953 | Hein, Jr. | |
| 2,655,604 A | 10/1953 | Hütter | |
| 2,680,439 A | 6/1954 | Sutermeister | |
| 3,859,996 A | 1/1975 | Mizzy et al. | |
| 4,059,107 A * | 11/1977 | Iriguchi et al. | 604/71 |
| D277,506 S | 2/1985 | Ibis | |
| 4,596,556 A | 6/1986 | Morrow et al. | |
| 4,739,973 A | 4/1988 | Herndon | |
| 4,790,824 A | 12/1988 | Morrow et al. | |
| 4,940,460 A | 7/1990 | Casey, I. et al. | |
| 4,941,880 A | 7/1990 | Burns | |
| 4,966,581 A | 10/1990 | Landau | |
| 5,064,413 A | 11/1991 | McKinnon et al. | |
| 5,312,335 A | 5/1994 | McKinnon et al. | |
| 5,312,577 A | 5/1994 | Peterson et al. | |
| D349,958 S | 8/1994 | Hollis et al. | |
| 5,383,851 A | 1/1995 | McKinnon, Jr. et al. | |
| 5,399,163 A | 3/1995 | Peterson et al. | |
| 5,466,220 A | 11/1995 | Brenneman | |
| 5,503,627 A | 4/1996 | McKinnon et al. | |
| 5,520,639 A | 5/1996 | Peterson et al. | |

(Continued)

FOREIGN PATENT DOCUMENTS

WO  WO00/33899  6/2000

(Continued)

OTHER PUBLICATIONS

MediFlo®—SureFlo® Valve Customer Engineering Drawing, Jun. 20, 2002, Liquid Molding Systems (Midland, MI).

*Primary Examiner*—Kevin C. Sirmons
*Assistant Examiner*—Andrew Gilbert
(74) *Attorney, Agent, or Firm*—Kolisch Hartwell, P.C.

(57) ABSTRACT

A needle-free injection device is described. The injection device typically includes a system for providing directed and pre-selected pressure and a nozzle with an orifice for defining a stream of fluid that is directed toward the skin of a patient against which a front end of the nozzle is positioned. The device also normally includes an engagement system that can selectively engage the nozzle with the pressurizing system so that the nozzle can be mounted to the pressurizing system to receive pressure for injection and so that after injection the nozzle can be removed and replaced for each new use of the device.

23 Claims, 19 Drawing Sheets

U.S. PATENT DOCUMENTS

| | | |
|---|---|---|
| 5,556,031 A | 9/1996 | Cooke et al. |
| 5,649,912 A | 7/1997 | Peterson |
| 5,746,714 A | 5/1998 | Salo et al. |
| 5,782,802 A | 7/1998 | Landau |
| D399,951 S | 10/1998 | Drach |
| 5,840,061 A | 11/1998 | Menne et al. |
| 5,865,795 A * | 2/1999 | Schiff et al. ................... 604/70 |
| 5,879,327 A | 3/1999 | Moreau DeFarges et al. |
| 5,891,086 A | 4/1999 | Weston |
| 5,893,397 A | 4/1999 | Peterson et al. |
| 5,993,412 A | 11/1999 | Deily et al. |
| 6,096,002 A | 8/2000 | Landau |
| 6,132,395 A | 10/2000 | Landau et al. |
| 6,168,587 B1 | 1/2001 | Bellhouse et al. |
| 6,264,629 B1 | 7/2001 | Landau |
| 6,319,224 B1 | 11/2001 | Stout et al. |
| 6,383,168 B1 | 5/2002 | Landau et al. |
| 6,471,669 B1 | 10/2002 | Landau |
| 6,475,181 B1 * | 11/2002 | Potter et al. ................... 604/68 |
| 6,506,177 B1 | 1/2003 | Landau |
| 6,544,084 B1 | 4/2003 | Nanami |
| 6,572,581 B1 | 6/2003 | Landau |
| 6,585,685 B1 | 7/2003 | Staylor et al. |
| 6,602,222 B1 | 8/2003 | Roser |
| 6,607,510 B1 | 8/2003 | Landau |
| 6,610,042 B1 | 8/2003 | Leon et al. |
| 6,802,826 B1 * | 10/2004 | Smoliarov et al. .......... 604/192 |
| 6,849,060 B1 * | 2/2005 | Brooks et al. ................ 604/58 |
| 2002/0087117 A1 | 7/2002 | Stout et al. |
| 2002/0123717 A1 | 9/2002 | Landau |
| 2002/0123718 A1 | 9/2002 | Landau |
| 2003/0065286 A1 | 4/2003 | Landau |
| 2003/0088214 A1 | 5/2003 | Leon et al. |
| 2003/0093030 A1 | 5/2003 | Landau |

FOREIGN PATENT DOCUMENTS

| | | |
|---|---|---|
| WO | WO00/48654 | 8/2000 |

* cited by examiner

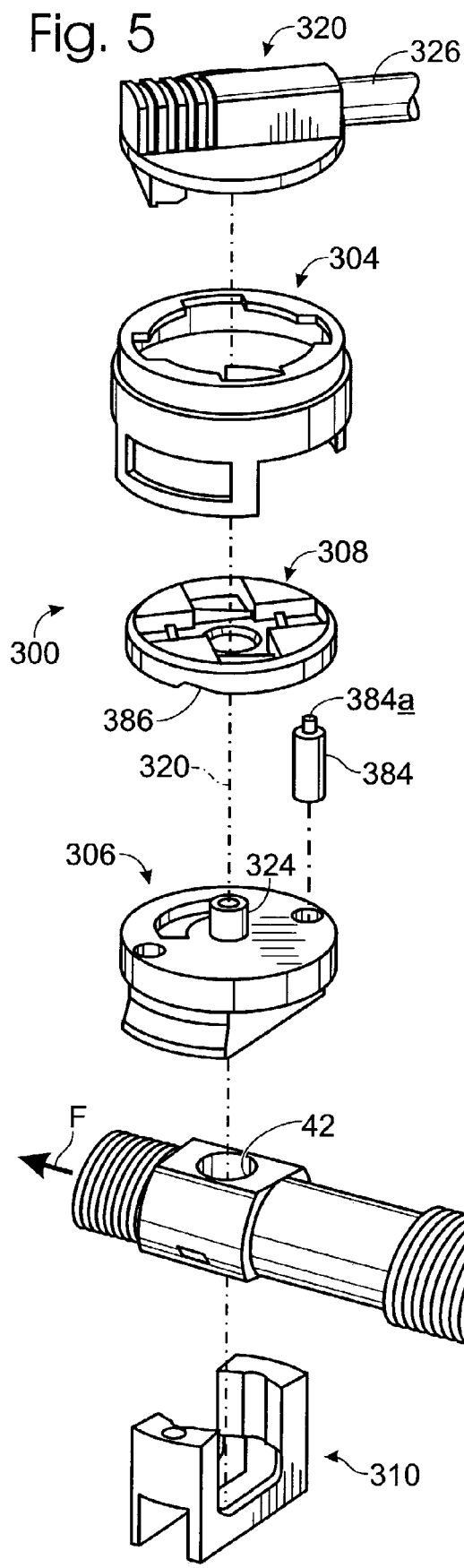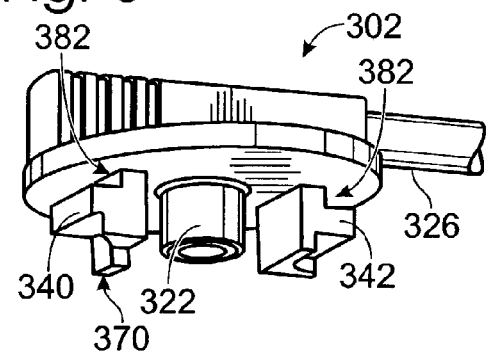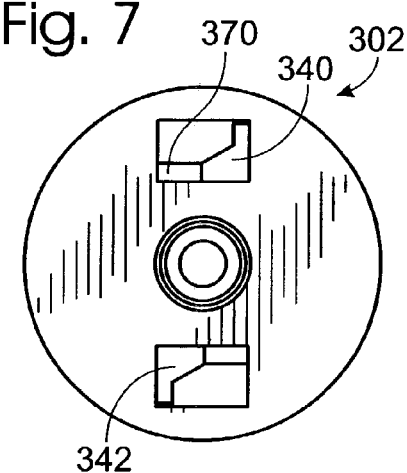

Fig. 8
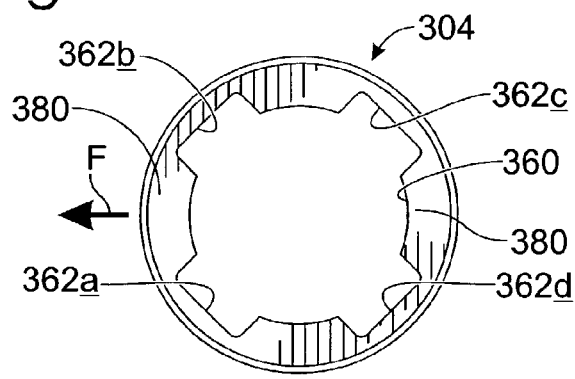
Fig. 9A       Fig. 9B       Fig. 9C
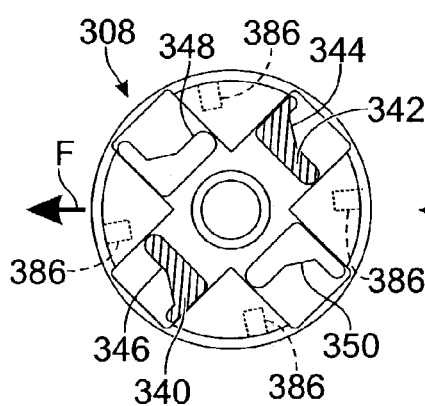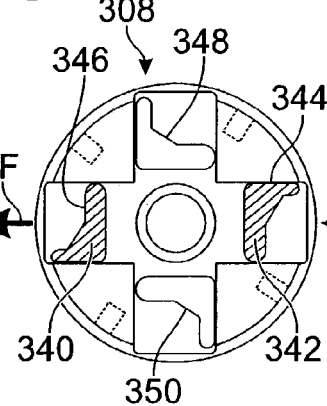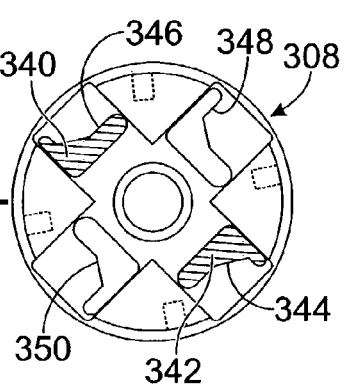
Fig. 10
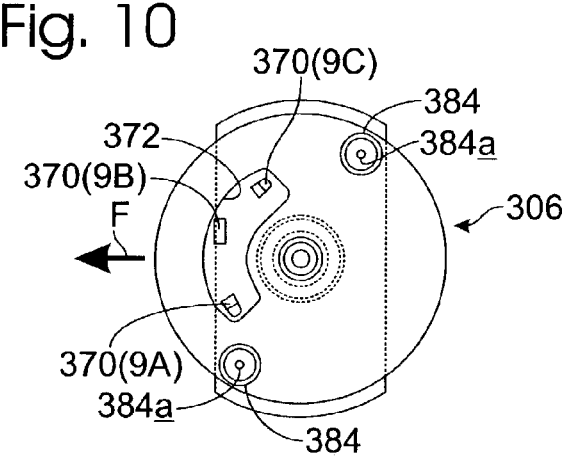

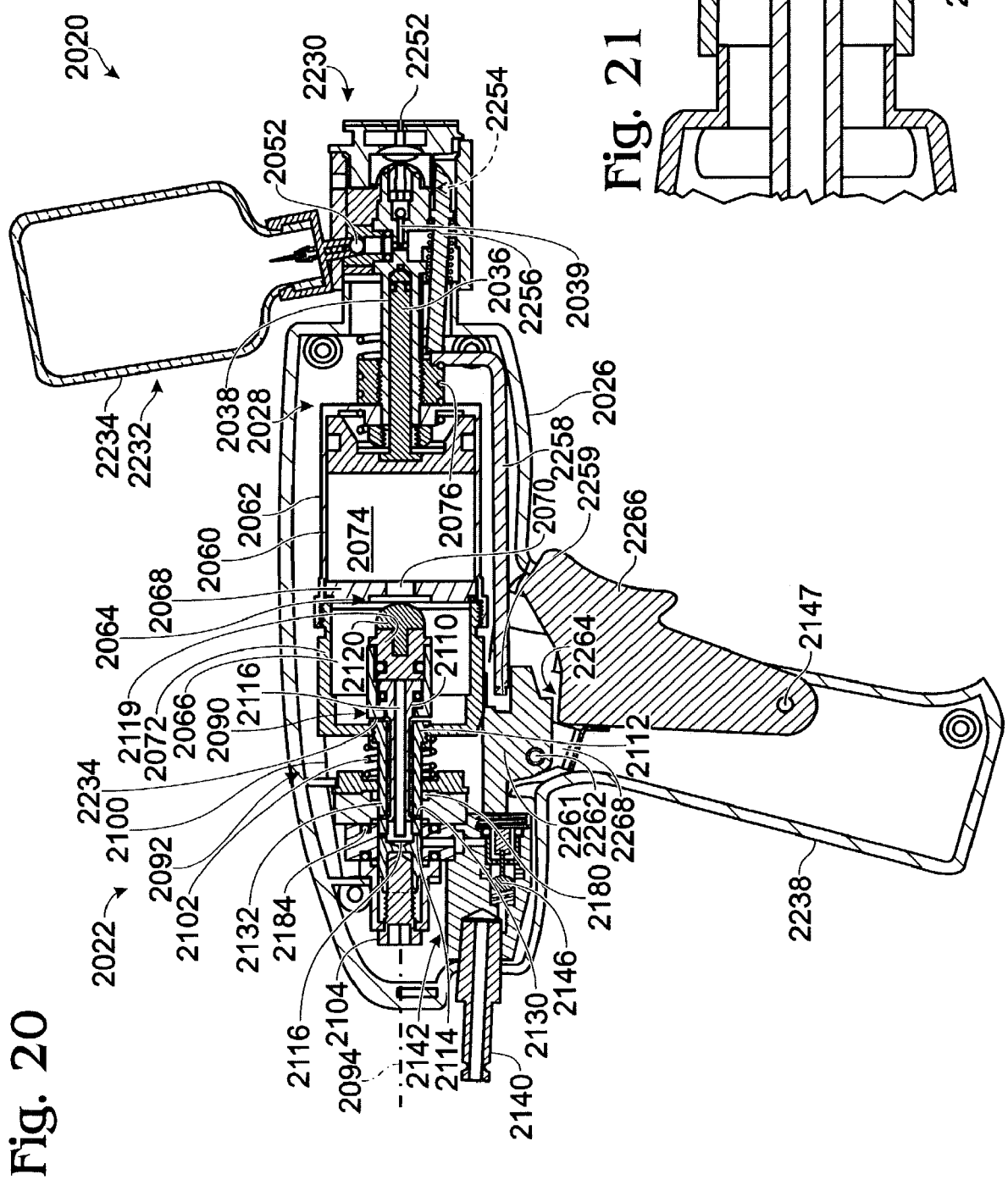
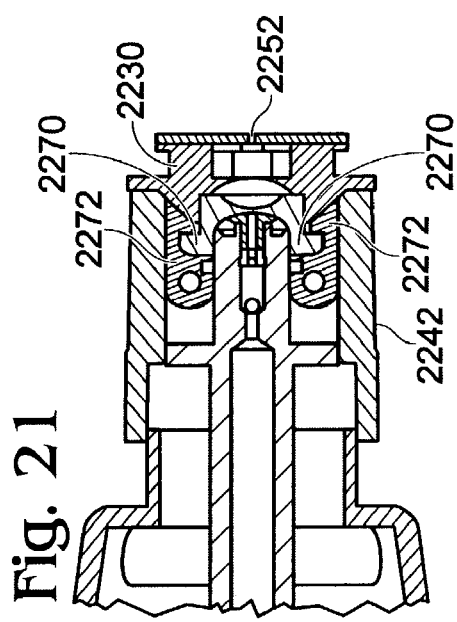
Fig. 20
Fig. 21

HIGH WORKLOAD NEEDLE-FREE INJECTION SYSTEM

CROSS REFERENCE TO RELATED APPLICATIONS

This application is a continuation-in-part of U.S. Pat. No. 6,676,630 Ser. No. 10/164,920, filed Jun. 4, 2002, the disclosure of which is incorporated in its entirety for all purposes.

BACKGROUND OF THE INVENTION

Needle-free injection systems provide an alternative to standard fluid delivery systems, which typically use a needle adapted to penetrate the outer surface of a target. Typically, needle-free injection systems are designed to eject the fluid from a fluid chamber with sufficient pressure to allow the fluid to penetrate the target to the desired degree. For example, common applications for needle-free injection systems include delivering intradermal, subcutaneous and intramuscular injections into or through a recipient's skin. For each of these applications, the fluid must be ejected from the system with sufficient pressure to allow the fluid to penetrate the tough exterior dermal layers of the recipient's skin.

SUMMARY OF THE INVENTION

The invention provides an improved needle-free injection device. The injection device includes a user-grippable housing and a syringe assembly movably secured to the housing. The syringe assembly is configured to expel injectable fluid out of a nozzle upon application of pressurized gas to the syringe assembly. The injection device also includes a pressurized gas delivery mechanism disposed within the housing and configured to selectively apply pressurized gas to the syringe assembly. The pressurized gas delivery mechanism is at least partly actuated by pressing the nozzle onto an injection site so that the syringe assembly moves relative to the housing.

BRIEF DESCRIPTION OF THE DRAWINGS

FIG. 5 is an isometric exploded view showing structures that may be used to connect a fluid supply to the injection device depicted in FIGS. 1–4.

FIG. 6 is an isometric view of a fluid supply adapter that is also shown in FIG. 5.

FIG. 7 is a bottom view of the fluid supply adapter shown in FIGS. 5 and 6.

FIG. 8 is a top view of a locking ring that is also shown in FIG. 5.

FIGS. 9A, 9B and 9C are top views of a rotatable key member that is also shown in FIG. 5, and show the rotatable key member in three different rotational positions relative to the injection device of FIGS. 1–4.

FIG. 10 is a top view of a base member that is also shown in FIG. 5.

FIG. 20 is a side sectional elevation view of the system of FIG. 16 that depicts the system in a fired position.

FIG. 21 is a partial top sectional view of the system of FIG. 16.

DETAILED DESCRIPTION OF THE PREFERRED EMBODIMENTS

Construction of the Preferred Embodiments

Figure 1:
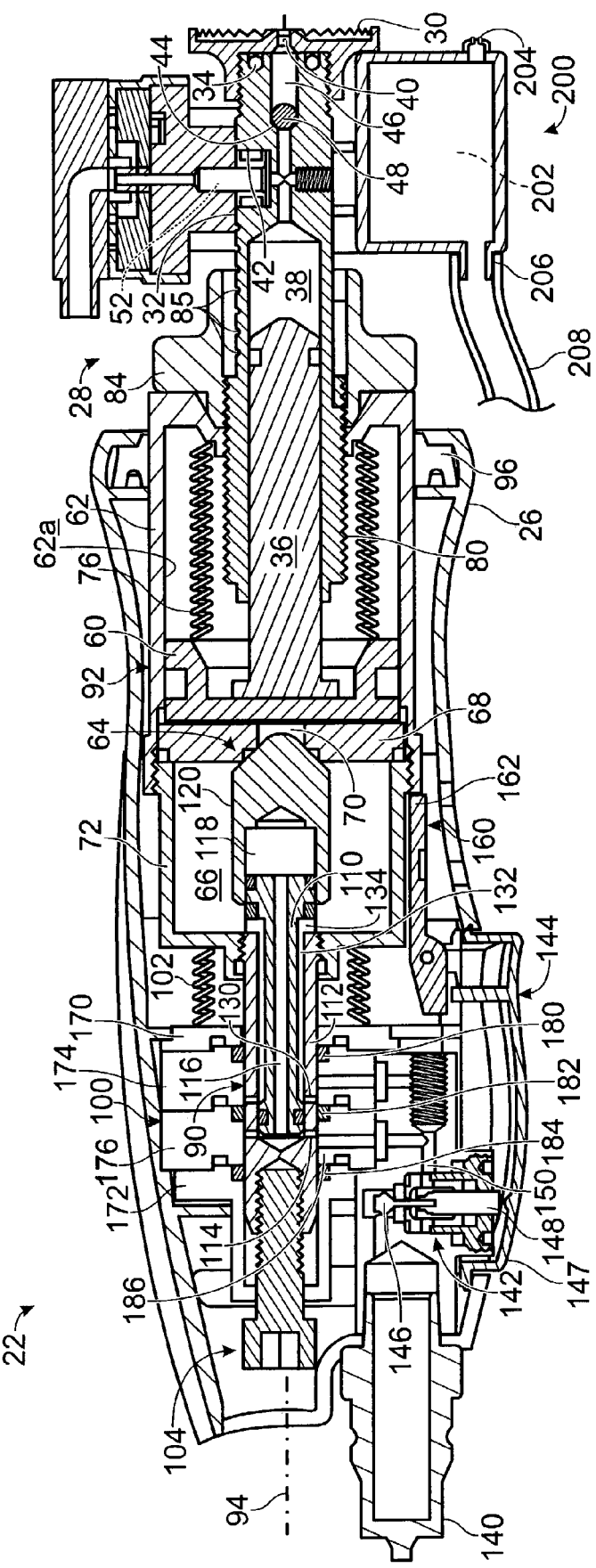
FIG. 1 is a sectional side elevation view of a needle-free injection system according to the invention, and depicts the system in a primed position.
Figure 2:
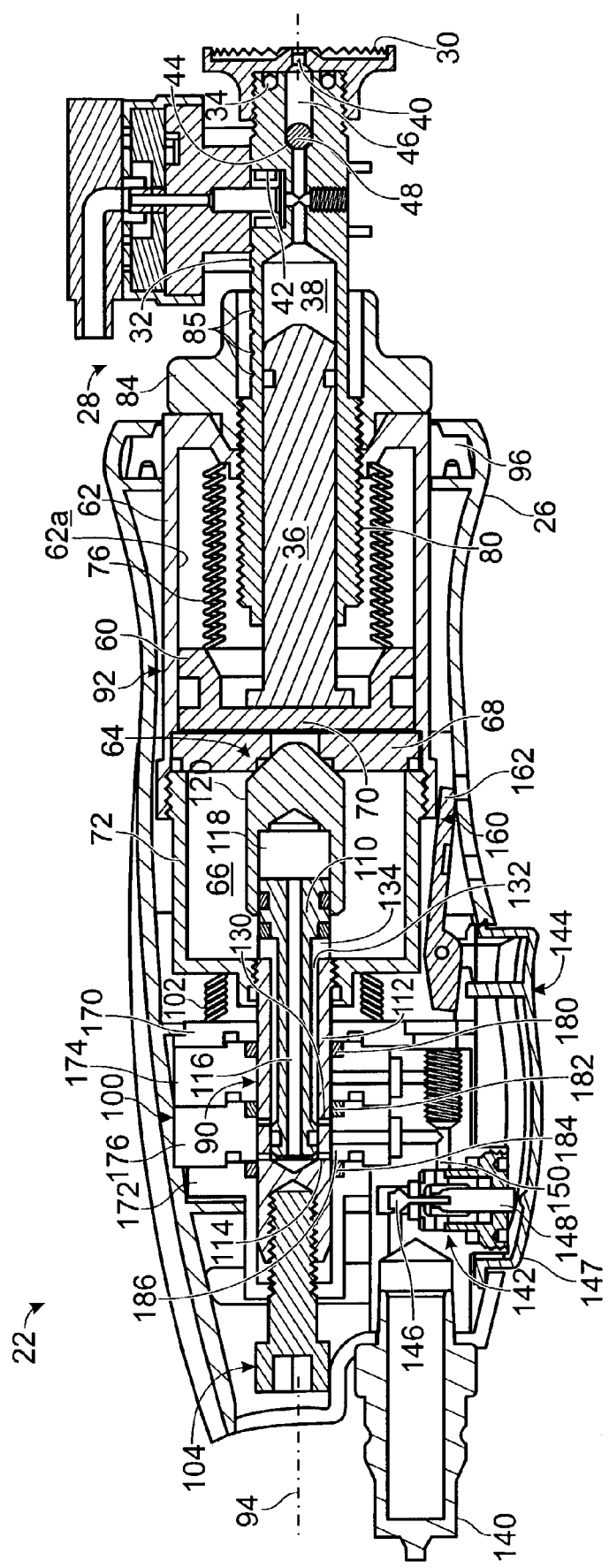
FIG. 2 is a sectional side elevation view of the system of FIG. 1 that depicts the system in a charged position.
Figure 3:
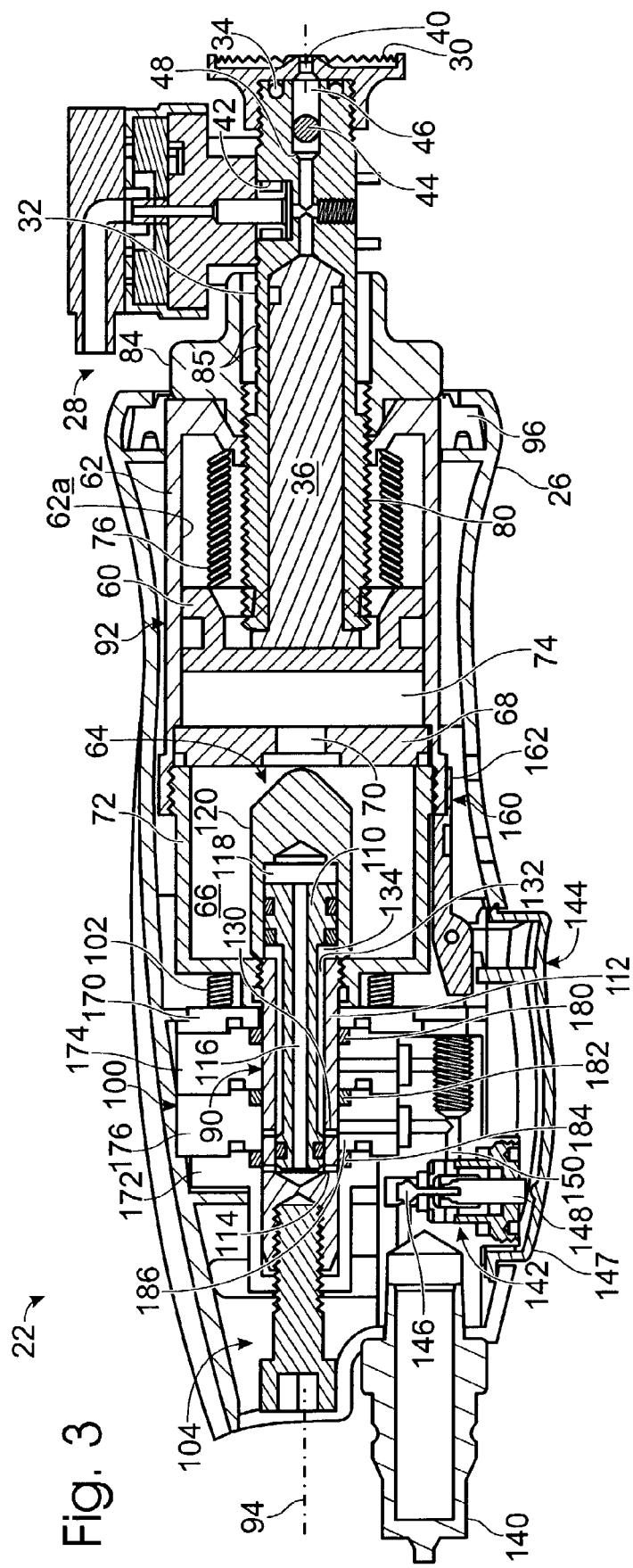
FIG. 3 is a sectional side elevation view of the system of FIG. 1 that depicts the system after it has been fired.
Figure 4:
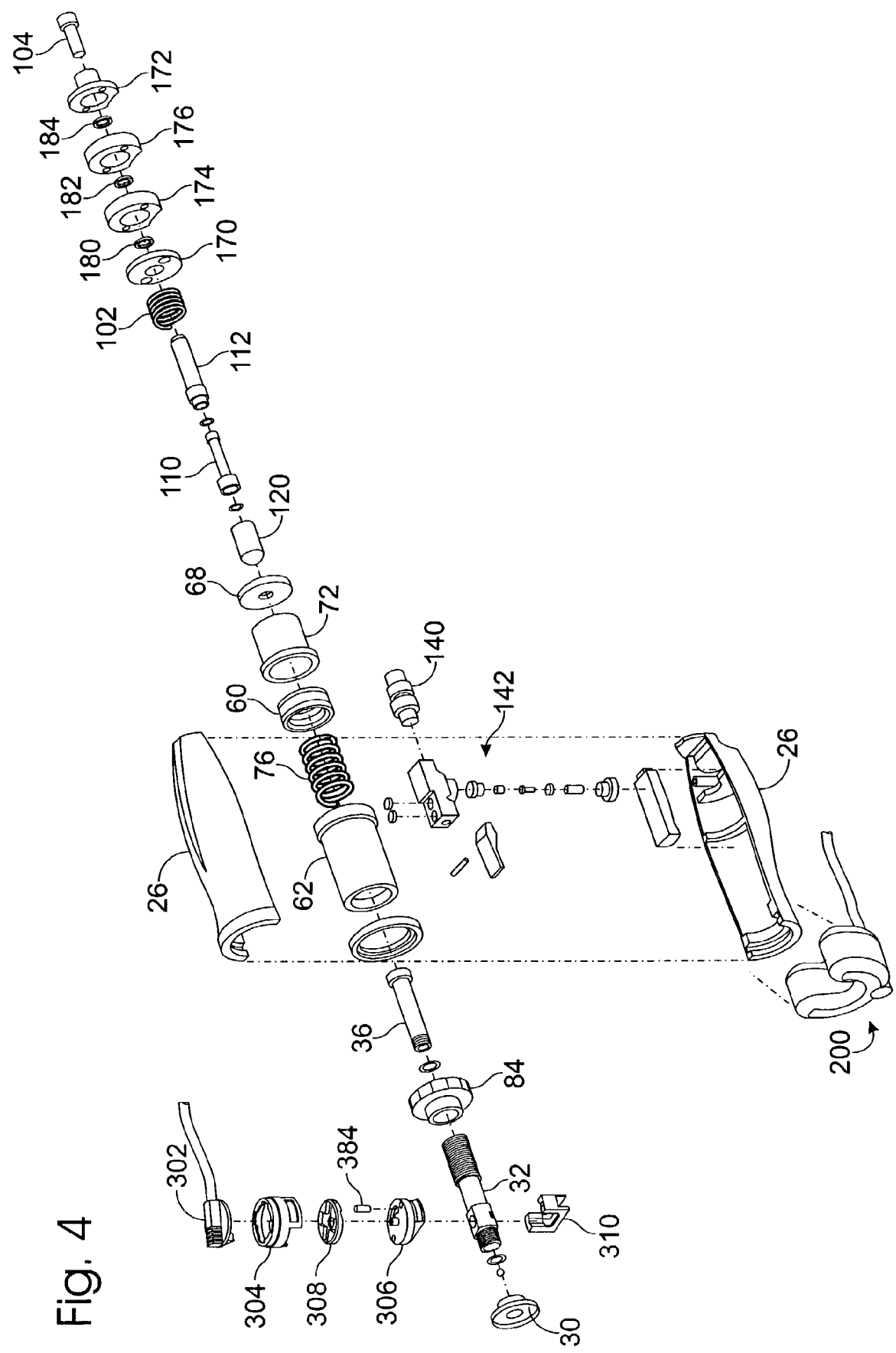
FIG. 4 is an exploded view of the system of FIG. 1.

FIG. 1 depicts a needle-free injection system 20 according to the invention, including an injection device 22. FIG. 1 shows injection device 22 in a first position, which will be referred to as the "primed" or "priming" position. Typically, the device is also placed in the position shown in FIG. 1 for storage and/or shipping. FIG. 2 depicts device 22 in a position which will be referred to as the "charged" or "charging" position; FIG. 3 depicts device 22 in a position which will be referred to as the "fired" or "firing" position. FIG. 4 is an exploded view depicting various components that may be used to construct injection device 22.

As will be explained in more detail below, injection device 22 is configured to inject a dose of a drug or other fluid into a subject animal. This is accomplished by using pressurized gas to expel fluid from the injection device. The pressurized gas may be supplied from a tank, cartridge or other source, and typically is delivered through device 22 and vented via operation of various valve structures. System 20 may include a fluid supply 24 that may be coupled with injection device 22 in order to supply the injection device with fluid, such as drugs, vaccines or other injectable fluids.

As shown, injection device 22 may include an outer housing 26, which typically is adapted to be comfortably held in a user's hand. The depicted housing is formed from injection-molded plastic, though various other materials and fabrication methods may be employed as desired.

Injection device 22 typically includes a fluid expulsion mechanism, such as syringe assembly 28, that is configured to draw in and forcibly expel drugs or other fluids. As shown in the figures, syringe assembly 28 may be disposed at least partially within housing 26 toward a forward end of the housing. Syringe assembly 28 includes a nozzle 30, which is affixed to an end of a fluid cylinder 32 and sealed thereon with an o-ring 34. A plunger 36 is slidably disposed within fluid cylinder 32, thereby defining a variable-volume fluid reservoir 38. When plunger 36 is advanced (i.e., moved to the right in FIGS. 1–3), fluid is expelled out of fluid reservoir 38 through a discharge outlet 40 provided in nozzle 30. Retraction of plunger 36 (i.e., moving the plunger to the left in FIGS. 1–3) draws fluid into fluid reservoir 38 through inlet 42, which typically is coupled with fluid supply 24. It should be appreciated that syringe assembly 28 is presented as an illustrative example only, and that other variable-volume devices may be employed. For example, a squeezable bulb or elastomeric bladder may be used to expel fluid from injection device 22.

In the depicted syringe assembly, outlet 40 and inlet 42 typically are provided with check valves to prevent backflow. Various types of valves may be used, though ball-type check valves have proved useful in the depicted embodiment. Specifically, as indicated in the figures, an outlet check ball 44 is disposed within an outlet check ball chamber 46. Outlet check ball 44 is held against a valve seat 48 as plunger 36 is retracted, to prevent fluid or contaminants from being drawn into fluid reservoir 38 through discharge outlet 40. A spring (not shown) may also be provided to urge the check ball to the left into the closed position. As plunger 36 advances, check ball 44 moves forward, away from engagement with seat 48, allowing fluid to pass around the check ball and out of nozzle 30 through outlet 40. Inlet 42 may also include a similar ball-type check valve 52, including a check ball (not shown) urged upward into a closed position against a valve seat. When plunger 36 retracts, check valve 52 opens, allowing fluid from fluid supply 24 to be drawn through the check ball valve into fluid reservoir 38.

As indicated, a piston 60 may be secured to plunger 36. In the depicted embodiment, piston 60 is slidably disposed within a piston cylinder 62, and creates a substantially sealed interface with an interior wall 62a of the piston cylinder. As will be explained in more detail below, when a poppet valve 64 opens, as shown in FIG. 3, pressurized gas from a gas reservoir 66 is allowed to escape past a gas bulkhead 68 through a bulkhead opening 70. Gas reservoir 66 is contained within a gas cylinder 72, which is fixedly secured relative to bulkhead 68 and piston cylinder 62. Upon the opening of poppet valve 64, the pressurized gas exerts upon operative surface 60a of piston 60, causing piston 60 and plunger 36 to advance forward and expel fluid from syringe assembly 28 through discharge outlet 40. The area between bulkhead 68 and piston 60 created by the advancement of piston 60 will be referred to as piston chamber 74 (FIG. 3). As indicated, a return spring 76 may be provided to urge piston 60 back toward bulkhead 68 upon venting of pressurized gas within piston chamber 74 and gas reservoir 66.

Syringe assembly 28 may be configured with an adjustment capability to allow variation of the maximum amount of fluid that may be drawn into and expelled from fluid reservoir 38. Specifically, as indicated, the outer circumference of fluid cylinder 32 may include threads 80 configured to interface with corresponding threads on piston cylinder 62. Rotation of the fluid cylinder then varies the plunger's permitted range of motion, by adjusting the maximum amount by which plunger 36 may be withdrawn from fluid cylinder 32 before being blocked by bulkhead 68. This adjusts the maximum volume of fluid reservoir 38. A locking nut 84 may also be provided to retain fluid cylinder 32 in place relative to piston cylinder 62 once a desired volume has been selected. Indicia 85 may be provided on the outer surface of the fluid cylinder 32, or in another suitable location, to indicate the selected volume and/or the relative position of fluid cylinder 32 and piston cylinder 62.

As indicated above, piston cylinder 62 typically is fixedly secured to gas bulkhead 68 and gas cylinder 72. Toward the rear half of housing 26, a slidable valve structure 90 is fixedly secured to gas cylinder 72. Piston cylinder 62, gas cylinder 72 and slidable valve structure 90 collectively form a reciprocating structure 92 which moves back and forth relative to housing 26 along axis 94. Syringe assembly 28 is secured to the forward end of reciprocating structure 92, and thus also moves relative to housing 26. The forward end of reciprocating structure 92 is held within an aperture in housing 26, such that at least part of syringe assembly 28 sticks out of the forward end of housing 26. A wiper seal 96 may be provided within the aperture to contact the reciprocating structure (e.g., the outer surface of piston cylinder 62). Toward the rear of reciprocating structure 92, slidable valve structure 90 is slidably supported within a valve body 100 that is fixedly secured within housing 26.

During operation, reciprocating structure 92 is progressively pushed into housing 26 from the position shown in FIG. 1, to the position shown in FIG. 3. Normally, this occurs as a result of pressing nozzle 30 against an injection site while manually gripping housing 26. Spring 102 is compressed as reciprocating structure 92 moves in a rearward direction relative to housing 26. Upon removal of the compressing force, spring 102 urges reciprocating structure 92 back toward the position shown in FIG. 1.

An adjustment bolt 104 or like device may be provided to adjust the degree to which reciprocating structure 92 may be pushed into housing 26. Specifically, as seen at the rear or left end of FIG. 3, the head of bolt 104 abuts the rear portion of the interior of housing 26 to prevent further rearward movement of reciprocating structure 92 relative to housing 26. Rotation of bolt 104 thus adjusts the available range of rearward travel of reciprocating structure 92.

As depicted, slidable valve structure 90 may include an inner valve sleeve 110 and an outer valve sleeve 112. In the depicted exemplary embodiment, outer valve sleeve 112 includes a first set of holes 114 which fluidly communicate with a bore passage 116 defined through the center of inner valve sleeve 110. Bore passage 116 fluidly couples with a poppet reservoir 118 defined in part by poppet 120. In the depicted embodiment, poppet 120 is slidably movable back and forth on the end of slidable valve structure 90. When poppet 120 is in its forward-most position, as shown in FIGS. 1 and 2, poppet 120 seats into a valve seat in bulkhead 68, thus sealing off gas reservoir 66 from piston chamber 74. Fore-and-aft movement of poppet 120 typically is controlled by gas pressure existing in poppet reservoir 118 and gas reservoir 66.

Outer valve sleeve 112 may include another set of holes 130, which fluidly communicate with a cylindrical passage 132. As indicated, passage 132 may be defined between the inner and outer valve sleeves. Cylindrical passage 132 fluidly couples with gas reservoir 66 via holes 134. The external surface of outer valve sleeve 112 may include a single, small groove 135 to provide a gas path between one of holes 130 and one of holes 114. This gas path provides a means of escape for exhaust gas at the conclusion of an injection sequence.

A gas fitting 140 may be provided into housing 26, to enable the injection device to be supplied with compressed air or some other pressurized gas via a gas hose (not shown). The delivery of pressurized gas through the device typically is controlled via a supply valve assembly 142, which is actuated via operation of a trigger 144. As shown, supply valve assembly 142 may include a valve 146 biased into a closed position by a spring (not shown), a supply valve plunger 148 secured to supply valve 146, and a supply conduit 150 through which pressurized gas is provided upon opening of the valve.

Trigger 144 is pivotally movable relative to housing 26 via a hinge 147 provided toward its rear end. Pushing the forward end of trigger 144 inward (or upward as depicted) causes valve plunger 148 to move upward. Upward movement of valve plunger 148 moves supply valve 146 upward into an open position, allowing pressurized gas to pass beyond supply valve 146 and be delivered to other parts of device 22 via a supply conduit 150.

Trigger 144 may also be used to operate a locking mechanism 160, which, when in the locked state shown in FIG. 1, prevents reciprocating structure 92 from being pushed into housing 26. Locking mechanism 160 includes a latch 162 pivotally connected within housing 26 and biased into the locking position by a spring (not shown). In addition to opening supply valve 146, pushing trigger 144 upward rotates latch 162 into an unlocked position, allowing reciprocating structure 92 to be moved rearward from the position shown in FIG. 1.

Valve body 100 includes a forward section 170, a rear section 172, and two intermediate sections 174 and 176. A spring 102 extends between and urges against forward section 170 and the rear end of gas cylinder 72. Three U-cup seals 180, 182 and 184 are provided between the pieces of the valve body. The area of intermediate section 176 between seals 182 and 184 provides a supply chamber 186 that is fluidly coupled with supply conduit 150 of supply valve assembly 142. The area of rear section 172 to the rear of seal 184 vents to atmosphere, as does the area of intermediate section 174 forward of seal 180.

Accordingly, it will be appreciated that moving slidable valve structure 90 backward and forward relative to valve body 100 (e.g., by pushing reciprocating structure 92 into housing 26) controls pressurization and venting of the various passages in slidable valve structure 90. Referring to FIG. 3, for example, valve structure 90 is positioned so that holes 114 in outer valve sleeve 112 are aligned slightly to the rear of seal 184, allowing bore passage 116 and poppet reservoir 118 to vent to atmosphere. In FIG. 1, holes 130 are aligned slightly to the front of seal 180, allowing cylindrical passage 132 and gas reservoir 66 to vent to atmosphere. In FIGS. 1–3, holes 114 and/or holes 130 are at times aligned with supply chamber 186, such that the respective passages and reservoirs are equalized in pressure relative to the supply chamber. Accordingly, in such a state of alignment, opening supply valve 146 would pressurize the respective passages/reservoirs.

As seen in FIG. 1, injection device 22 may also include a dye marker 200. Dye marker 200 includes a dye reservoir 202 and a dye outlet 204. A pressure inlet 206 is coupled with a pressure source via a hose 208. Dye marker 200 is configured to apply a metered amount of marking dye to an injection site upon application of air pressure through hose 208. Typically, the pressure source is provided by the residual air pressure in gas reservoir 66 and piston chamber 74 as those areas are vented. Specifically, hose 208 may be coupled to an exhaust port in housing 26 to fluidly couple dye marker 200 with venting passages within injection device 22.

Figure 11:
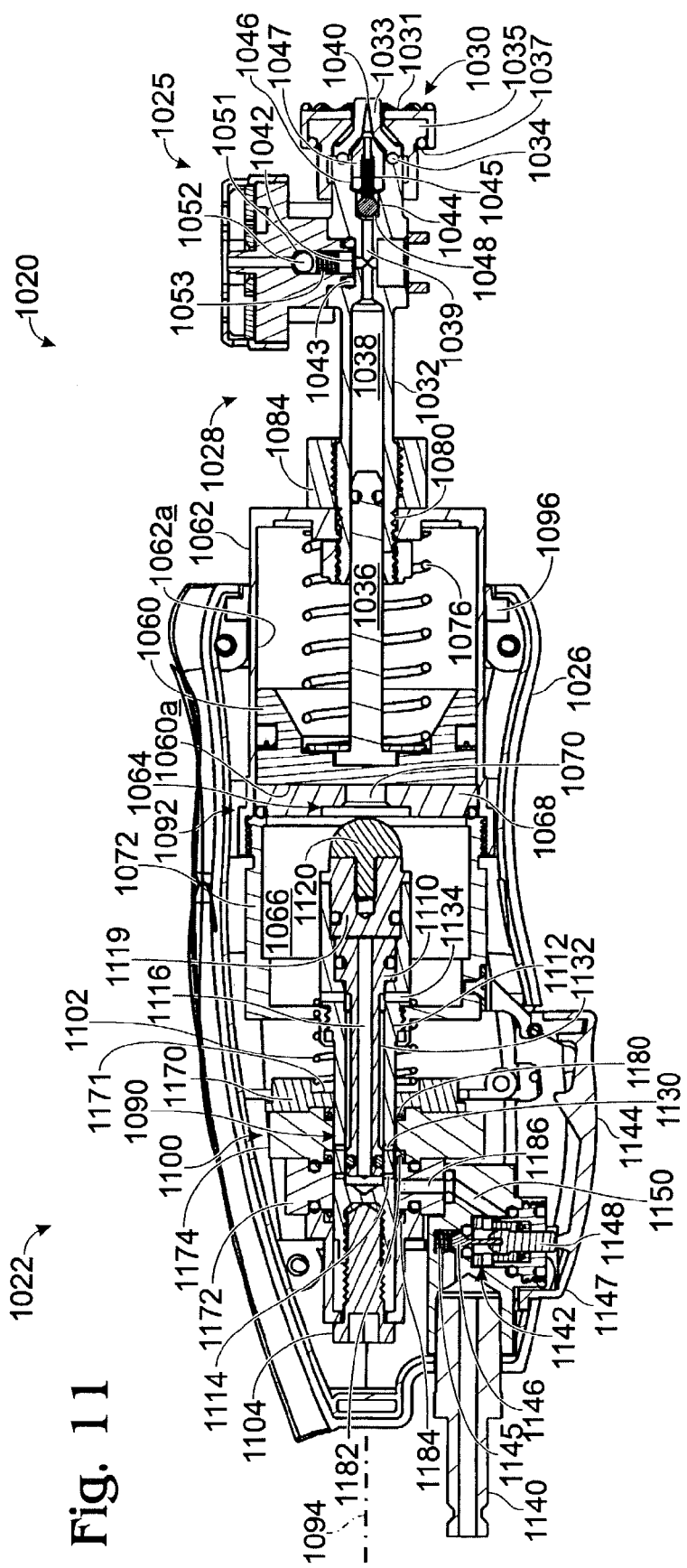
FIG. 11 is a sectional side elevation view of a needle-free injection system according to another embodiment of the invention, and depicts the system in a primed position.
Figure 12:
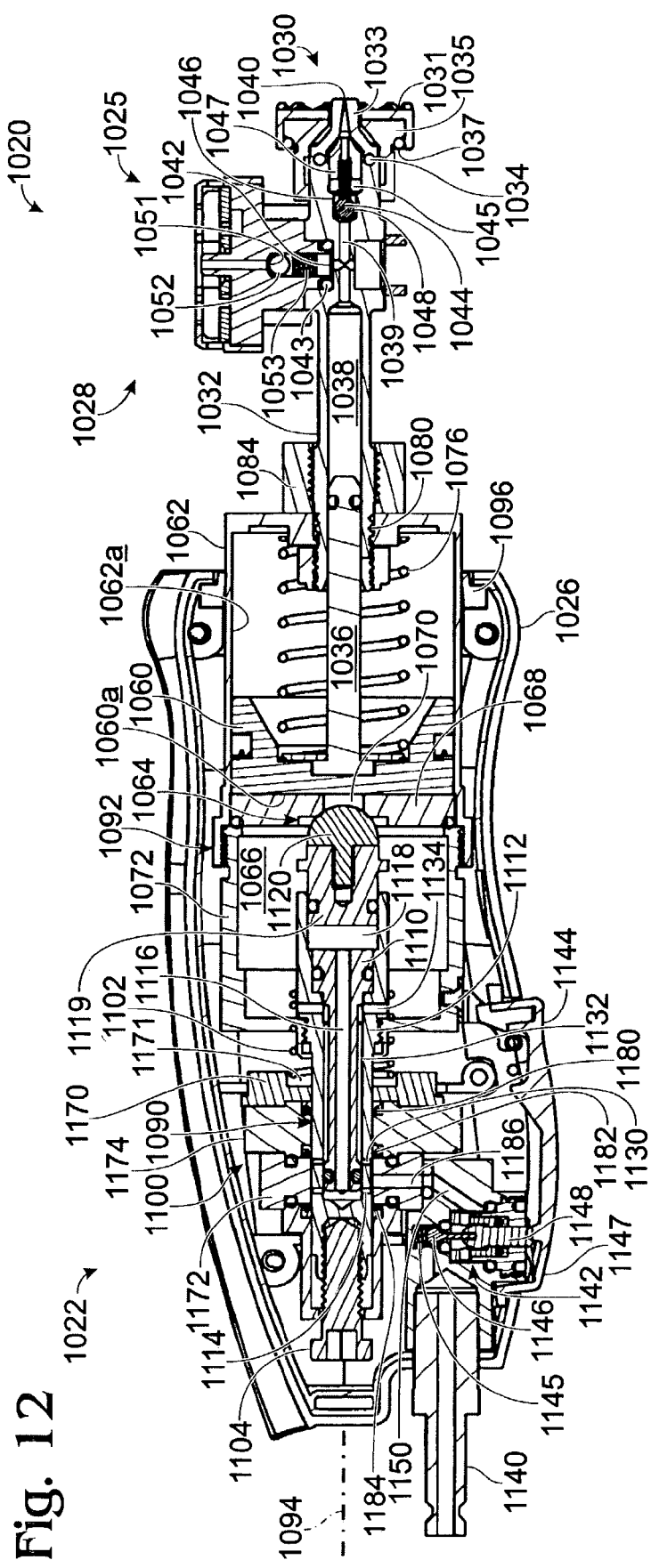
FIG. 12 is a sectional side elevation view of the system of FIG. 11 that depicts the system in a charged position.
Figure 13:
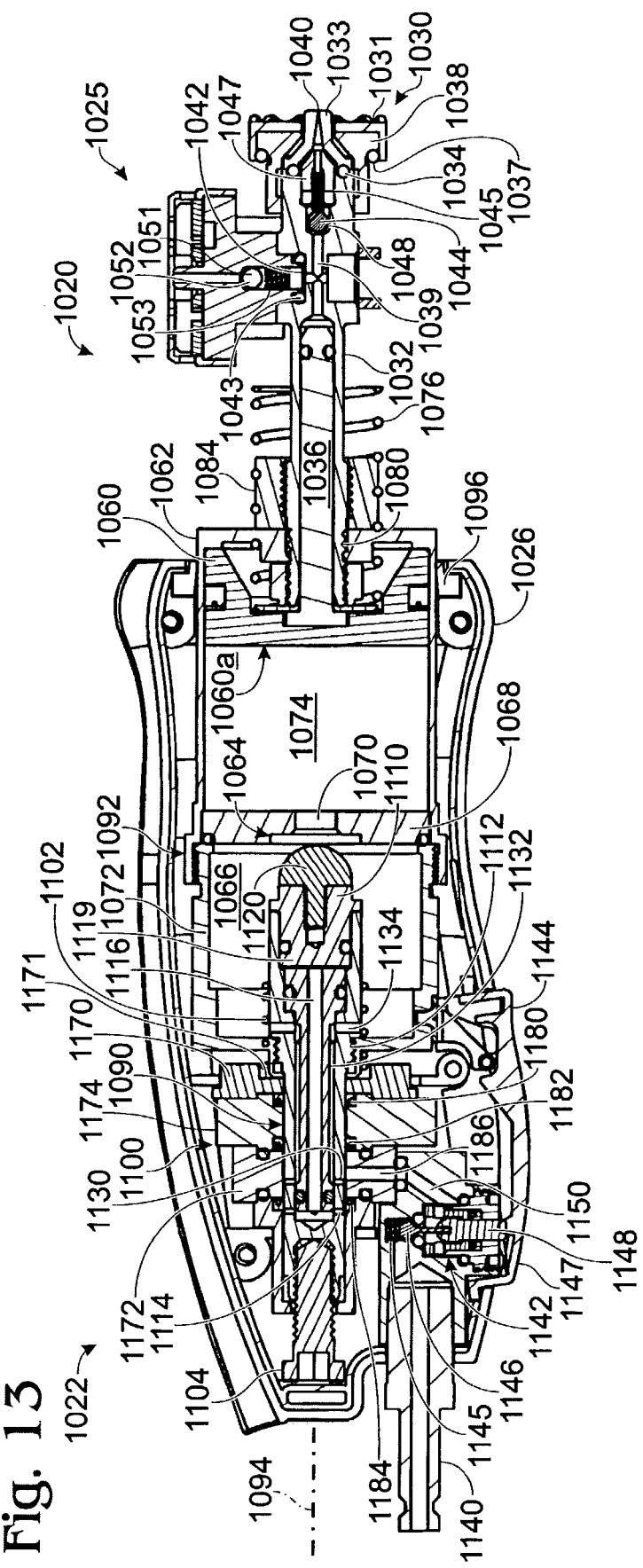
FIG. 13 is a sectional side elevation view of the system of FIG. 11 that depicts the system after it has been fired.
Figure 14:
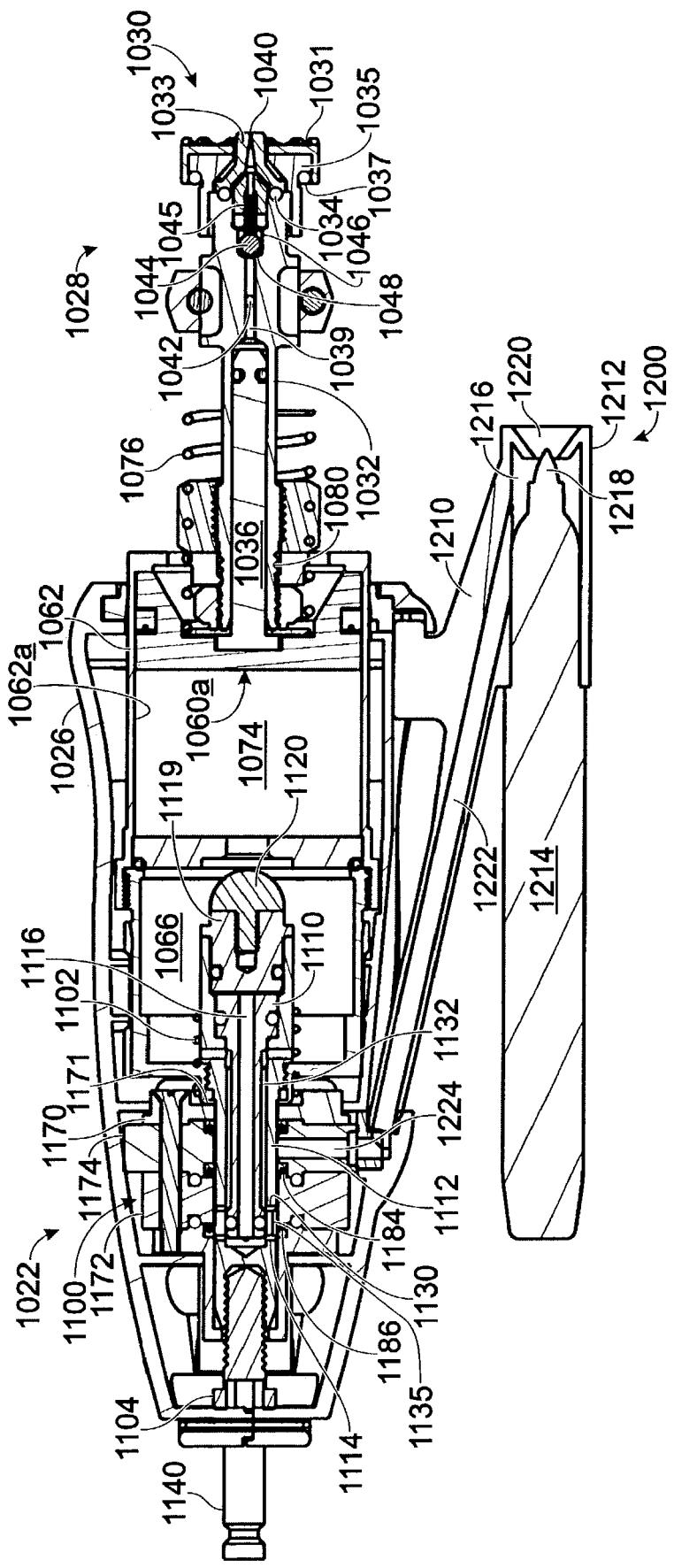
FIG. 14 is a sectional top view of the system of FIG. 11 that depicts the system in a primed position.
Figure 15:
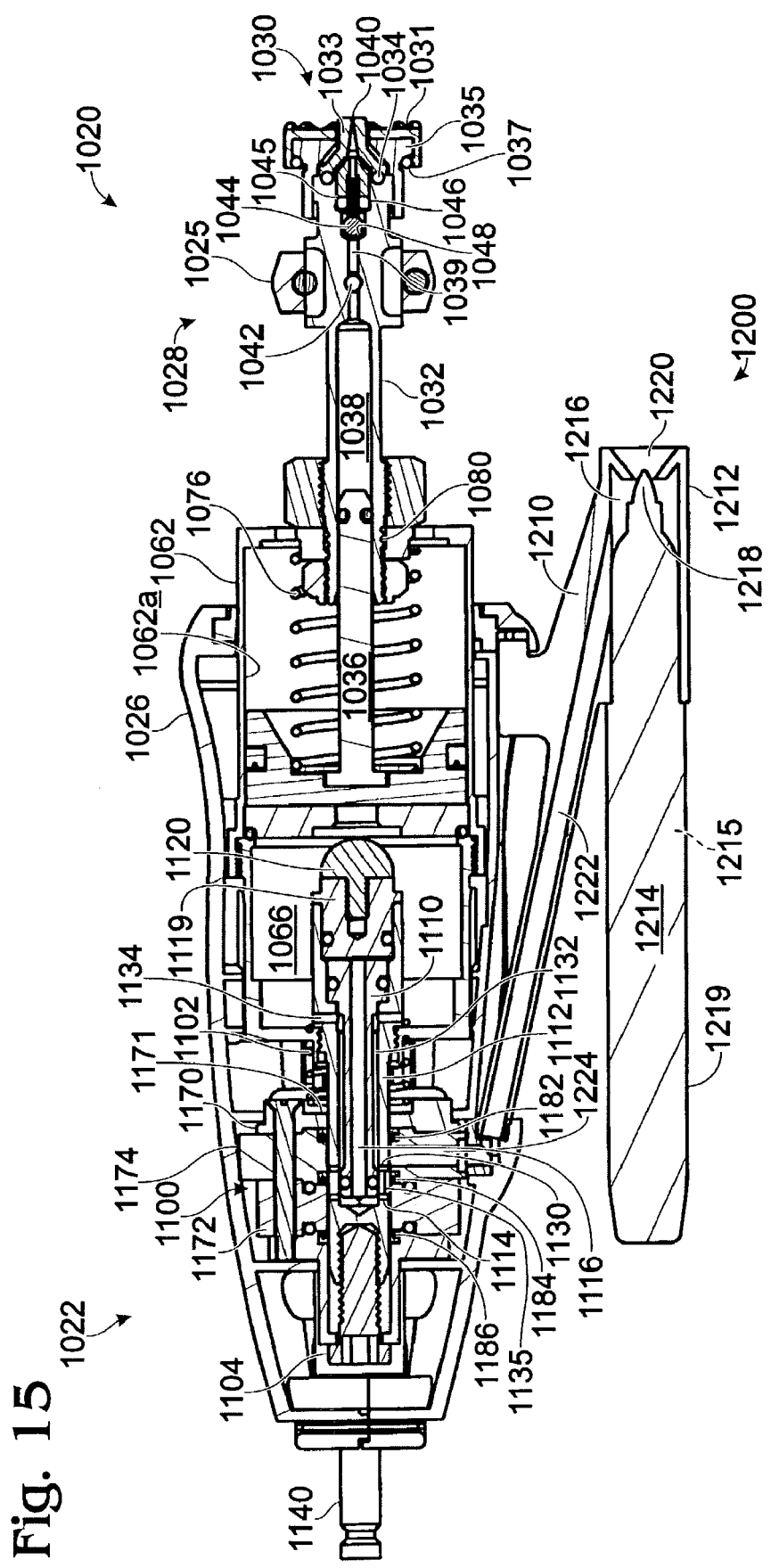
FIG. 15 is a sectional top view of the system of FIG. 11 that depicts the system after it has been fired.

FIGS. 11–15 depict a needle-free injection system 1020 according to another embodiment of the invention. Injection system 1020 includes an injection device 1022. FIG. 11 shows injection device 1022 in a first position. Typically, the device is placed in the position shown in FIG. 11 for storage and/or shipping, and thus, this position may be referred to as the "storage" position. FIG. 12 depicts device 1022 in a position which will be referred to as the "primed," or "priming" position. FIG. 13 depicts device 1022 in a position which will be referred to as the "fired" or "firing" position. FIG. 14 depicts device 1022 in the storage position shown in FIG. 11, but rotated 90 degrees along the horizontal axis to show a top sectional view. FIG. 15 depicts device 1022 in the fired position shown in FIG. 13, but rotated 90 degrees along the horizontal axis to show a top sectional view.

For the sake of clarity those elements of the injection device shown in FIGS. 11–15 that perform the same or a similar function as elements of the injection device described with respect to FIGS. 1–3 are given corresponding reference numbers in the thousands range. For example, where the injection device in FIGS. 1–3 is given the reference number 22, the injection device in FIGS. 11–15 is given the reference number 1022. Moreover, it should be appreciated that any of the elements described with respect to the embodiment shown in FIGS. 1–3 may be incorporated into the device shown in FIGS. 11–15 and vice versa.

As in the embodiment described above with respect to FIGS. 1–3, injection device 1022 is configured to inject a dose of a drug or other fluid into a subject animal. This is accomplished by using pressurized gas to expel fluid from the injection device. The pressurized gas may be supplied from a tank, cartridge or other source, and typically is delivered through device 1022 and vented via operation of various valve structures. System 1020 may include a fluid supply (not shown) that may be coupled with injection device 1022 in order to supply the injection device with fluid, such as drugs, vaccines or other injectable fluids.

As shown, injection device 1022 may include an outer housing 1026, which typically is adapted to be comfortably held in a user's hand. The depicted housing is formed from injection-molded plastic, though various other materials and fabrication methods may be employed as desired.

Injection device 1022 typically includes a fluid expulsion mechanism, such as syringe assembly 1028, that is configured to draw in and forcibly expel drugs or other fluids. As shown in the figures, syringe assembly 1028 may be disposed at least partially within housing 1026 toward a forward end of the housing. Syringe assembly 1028 includes a disposable nozzle assembly 1030. Detachable nozzle assembly 1030 includes a disposable end cap 1031 and a disposable nozzle 1033. End cap 1031 is detachably connected to a retaining structure 1035, and may be sealed thereon by an o-ring 1037. Nozzle 1033 may be detachably seated into retaining structure 1035, and defines discharge outlet 1040.

O-ring 1034 may provide a seal between disposable nozzle 1033 and fluid cylinder 1032. End cap 1031, nozzle 1033, and retaining structure 1035 may be formed out of any suitable material or materials including, for example, plastic or metal. In some embodiments, end cap 1031 and nozzle 1033 may be formed of plastic, while retaining structure 1035 may be formed of metal.

A plunger 1036 is slidably disposed within fluid cylinder 1032, thereby defining a variable-volume fluid reservoir 1038. When plunger 1036 is advanced (i.e., moved to the right in FIGS. 11–14), fluid is expelled out of fluid reservoir 1038 via fluid path 1039 and through a discharge outlet 1040 provided in nozzle 1030. Retraction of plunger 1036 (i.e., moving the plunger to the left in FIGS. 11–15) draws fluid into fluid reservoir 1038 through inlet 1042, which typically is coupled with a fluid supply via connecting assembly 1025. The connection between inlet 1042 and fluid path 1039 may be sealed by an o-ring 1043. It should be appreciated that syringe assembly 1028 is presented as an illustrative example only, and that other variable-volume devices may be employed. For example, a squeezable bulb or elastomeric bladder may be used to expel fluid from injection device 1022.

In the depicted syringe assembly, outlet 1040 and inlet 1042 typically are provided with check valves to prevent backflow. Various types of valves may be used, including ball-type check valves. Specifically, as indicated in the figures, an outlet check ball 1044 is disposed within an outlet check ball chamber 1046. Outlet check ball 1044 is held against a valve seat 1048 as plunger 1036 is retracted, to prevent fluid or contaminants from being drawn into fluid reservoir 1038 through discharge outlet 1040. A spring 1045 may also be provided to urge the check ball towards valve seat 1048 and into the closed position. Spring 1045 may be retained in place by a retaining structure 1047. Retaining structure 1047 may, for example, be formed of plastic or any other suitable material. As plunger 1036 advances, check ball 1044 moves forward, away from engagement with seat 1048, allowing fluid to pass around the check ball and out of nozzle 1030 through outlet 1040. Inlet 1042 may also include a similar ball-type check valve including a check ball 1052 urged upward into a closed position against a valve seat 1051. Again, a spring 1053 may be provided to urge check ball 1052 into valve seat 1051 and into the closed position. When plunger 1036 retracts, check valve 1052 opens, allowing fluid from fluid supply 1024 to be drawn through the check ball valve into fluid reservoir 1038.

As indicated, a piston 1060 may be secured to plunger 1036. In the depicted embodiment, piston 1060 is slidably disposed within a piston cylinder 1062, and creates a substantially sealed interface with an interior wall 1062a of the piston cylinder. As will be explained in more detail below, when a poppet valve 1064 opens, as shown in FIG. 13, pressurized gas from a gas reservoir 1066 is allowed to escape past a gas bulkhead 1068 through a bulkhead opening 1070. Gas reservoir 1066 is contained within a gas cylinder 1072, which is fixedly secured relative to bulkhead 1068 and piston cylinder 1062. Upon the opening of poppet valve 1064, the pressurized gas exerts upon operative surface 1060a of piston 1060, causing piston 1060 and plunger 1036 to advance forward and expel fluid from syringe assembly 1028 through discharge outlet 1040. The area between bulkhead 1068 and piston 1060 created by the advancement of piston 1060 will be referred to as piston chamber 1074 (FIG. 13). As indicated, a return spring 1076 may be provided to urge piston 1060 back toward bulkhead 1068 upon venting of pressurized gas within piston chamber 1074 and gas reservoir 1066.

Syringe assembly 1028 may be configured with an adjustment capability to allow variation of the maximum amount of fluid that may be drawn into and expelled from fluid reservoir 1038. Specifically, as indicated, the outer circumference of fluid cylinder 1032 may include threads 1080 configured to interface with corresponding threads on piston cylinder 1062. Rotation of the fluid cylinder then varies the plunger's permitted range of motion, by adjusting the maximum amount by which plunger 1036 may be withdrawn from fluid cylinder 1032 before being blocked by bulkhead 1068. This adjusts the maximum volume of fluid reservoir 1038. A locking nut 1084 may also be provided to retain fluid cylinder 1032 in place relative to piston cylinder 1062 once a desired volume has been selected. While not shown, as with the embodiment described with respect to FIGS. 1–3, indicia may be provided on the outer surface of the fluid cylinder 1032, or in another suitable location, to indicate the selected volume and/or the relative position of fluid cylinder 1032 and piston cylinder 1062.

As indicated above, piston cylinder 1062 typically is fixedly secured to gas bulkhead 1068 and gas cylinder 1072. Toward the rear half of housing 1026, a slidable valve structure 1090 is fixedly secured to gas cylinder 1072. Piston cylinder 1062, gas cylinder 1072 and slidable valve structure 1090 collectively form a reciprocating structure 1092 which moves back and forth relative to housing 1026 along axis 1094. Syringe assembly 1028 is secured to the forward end of reciprocating structure 1092, and thus also moves relative to housing 1026. The forward end of reciprocating structure 1092 is held within an aperture in housing 1026, such that at least part of syringe assembly 1028 sticks out of the forward end of housing 1026. A wiper seal 1096 may be provided within the aperture to contact the reciprocating structure (e.g., the outer surface of piston cylinder 1062). Toward the rear of reciprocating structure 1092, slidable valve structure 1090 is slidably supported within a valve body 1100 that is fixedly secured within housing 1026.

During operation, reciprocating structure 1092 is progressively pushed into housing 1026 from the position shown in FIG. 11, to the position shown in FIG. 13. Normally, this occurs as a result of pressing nozzle 1030 against an injection site while manually gripping housing 1026. Spring 1102 is compressed as reciprocating structure 1092 moves in a rearward direction relative to housing 1026. Upon removal of the compressing force, spring 1102 urges reciprocating structure 1092 back toward the position shown in FIG. 11.

An adjustment bolt 1104 or like device may be provided to adjust the degree to which reciprocating structure 1092 may be pushed into housing 1026. Specifically, as seen at the rear or left end of FIG. 13, the head of bolt 1104 abuts the rear portion of the interior of housing 1026 to prevent further rearward movement of reciprocating structure 1092 relative to housing 1026. Rotation of bolt 1104 thus adjusts the available range of rearward travel of reciprocating structure 1092.

As depicted, slidable valve structure 1090 may include an inner valve sleeve 1110 and an outer valve sleeve 1112. In the depicted exemplary embodiment, outer valve sleeve 1112 includes a first set of holes 1114 which fluidly communicate with a bore passage 1116 defined through the center of inner valve sleeve 1110. Bore passage 1116 fluidly couples with a poppet reservoir 1118 defined in part by poppet seat 1119. Poppet seat 1119 is adapted to retain a poppet 1120. In the depicted embodiment, poppet seat 1119 is slidably movable back and forth on the end of slidable valve structure 1090. When poppet seat 1119 is in its forward-most position, as shown in FIG. 12, poppet 1120 seats into a valve seat in bulkhead 1068, thus sealing off gas reservoir 1066 from piston chamber 1074. Fore-and-aft movement of poppet seat 1119 typically is controlled by gas pressure existing in poppet reservoir 1118 and gas reservoir 1066.

Outer valve sleeve 1112 may include another set of holes 1130, which fluidly communicate with a cylindrical passage 1132. As indicated, passage 1132 may be defined between the inner and outer valve sleeves. Cylindrical passage 1132 fluidly couples with gas reservoir 1066 via holes 1134. The external surface of the outer valve sleeve 1112 may include a single, small groove, 1135 (shown in FIGS. 14 and 15) to provide a gas path between one of holes 130 and one of holes 114. This gas path provides a means of escape for exhaust gas at the conclusion of an injection sequence.

A gas fitting 1140 may be provided into housing 1026, to enable the injection device to be supplied with compressed air or some other pressurized gas via a gas hose (not shown). The delivery of pressurized gas through the device typically is controlled via a supply valve assembly 1142, which is actuated via operation of a trigger 1144. As shown, supply valve assembly 1142 may include a valve 1146 biased into a closed position by a spring 1145, a supply valve plunger 1148 secured to supply valve 1146, and a supply conduit 1150 through which pressurized gas is provided upon opening of the valve.

Trigger 1144 is pivotally movable relative to housing 1026 via a hinge 1147 provided toward its rear end. Pushing the forward end of trigger 1144 inward (or upward as depicted) causes valve plunger 1148 to move upward. Upward movement of valve plunger 1148 moves supply valve 1146 upward into an open position, allowing pressurized gas to pass beyond supply valve 1146 and be delivered to other parts of device 1022 via a supply conduit 1150.

Valve body 1100 includes a forward section 1170, a rear section 1172, and an intermediate section 1174. A spring 1102 extends between and urges against a recessed region 1171 of forward section 1170 and the rear end of gas cylinder 1072. Three U-cup seals 1180, 1182 and 1184 are provided between the pieces of the valve body. The area of rear section 1172 between seals 1182 and 1184 provides a supply chamber 1186 that is fluidly coupled with supply conduit 1150 of supply valve assembly 1142.

Accordingly, it will be appreciated that moving slidable valve structure 1090 backward and forward relative to valve body 1100 (e.g., by pushing reciprocating structure 1092 into housing 1026) controls pressurization and venting of the various passages in slidable valve structure 1090. Referring to FIG. 13, for example, valve structure 1090 is positioned so that holes 1114 in outer valve sleeve 1112 are aligned slightly to the rear of seal 1184, allowing bore passage 1116 and poppet reservoir 1118 to vent to atmosphere. In FIG. 11, holes 1130 are aligned slightly to the front of seal 1182, allowing cylindrical passage 1132 and gas reservoir 1066 to vent to atmosphere. In FIGS. 11–13, holes 1114 and/or holes 1130 are at times aligned with supply chamber 1186, such that the respective passages and reservoirs are equalized in pressure relative to the supply chamber. Accordingly, in such a state of alignment, opening supply valve 1146 would pressurize the respective passages/reservoirs.

As seen in FIGS. 14 and 15, injection device 1022 may also include a marking assembly 1200. Marking assembly 1200 is connected to outer housing 1026 of device 1022 by supporting structure 1210. As shown, supporting structure 1210 may terminate in a housing 1212, which is adapted to receive and secure a fluid reservoir 1214. Typically, fluid reservoir 1214 includes a fluid chamber 1215 in fluid communication with a nib 1218, which extends out of the fluid chamber. Nib 1218 typically acts as a wick, drawing fluid out of reservoir 1214. Typically, reservoir 1214 holds ink or some other fluid capable of leaving a detectable mark on the surface (i.e., skin, hide, or hair) of an injection recipient. In the depicted embodiment, fluid reservoir 1214 may take the form of a writing instrument, or marker 1219. Suitable markers include the Sharpie® writing instruments sold by Sanford Corp. (Bellwood, Ill.).

As shown, housing 1212 defines a chamber 1216 near nib 1218 of marker 1202. Chamber 1216 includes an outlet 1220, surrounding nib 1218. Outlet 1220 may, for example, be conical in shape, extending from nib 1218 outwards, as shown, thereby creating a shaped venture channel. Air passage 1222 extends from chamber 1216 through supporting structure 1210 and into device 1022, where it communicates with supply conduit 1224. Supply conduit 1224 is adapted to communicate with holes 1130 in slidable valve structure 1090 when the slidable valve structure is moved from the fired position (shown in FIG. 14) to the storage position (shown in FIG. 15). Thus, after an injection, at least a portion of the exhaust gas in gas reservoir 1066 and piston chamber 1074 may be vented into chamber 1216, such that the airflow through chamber 1216 is directed past nib 1218, drawing fluid from nib 1218 out of outlet 1220 and onto the surface of the injection recipient.

Figure 16:
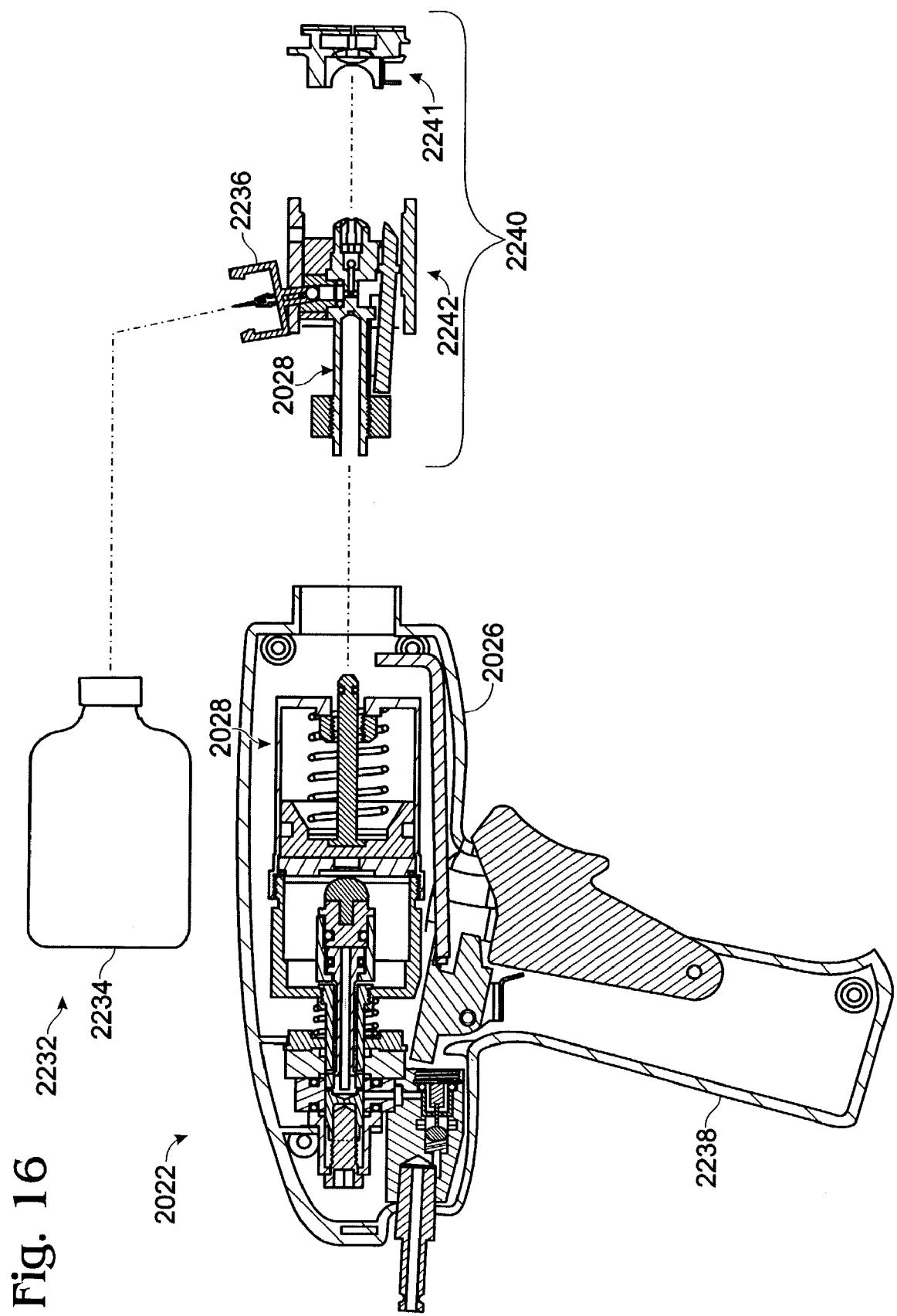
FIG. 16 is a sectional side elevation view of a needle-free injection system according to another embodiment of the invention, and depicts the system in a disassembled position.
Figure 17:
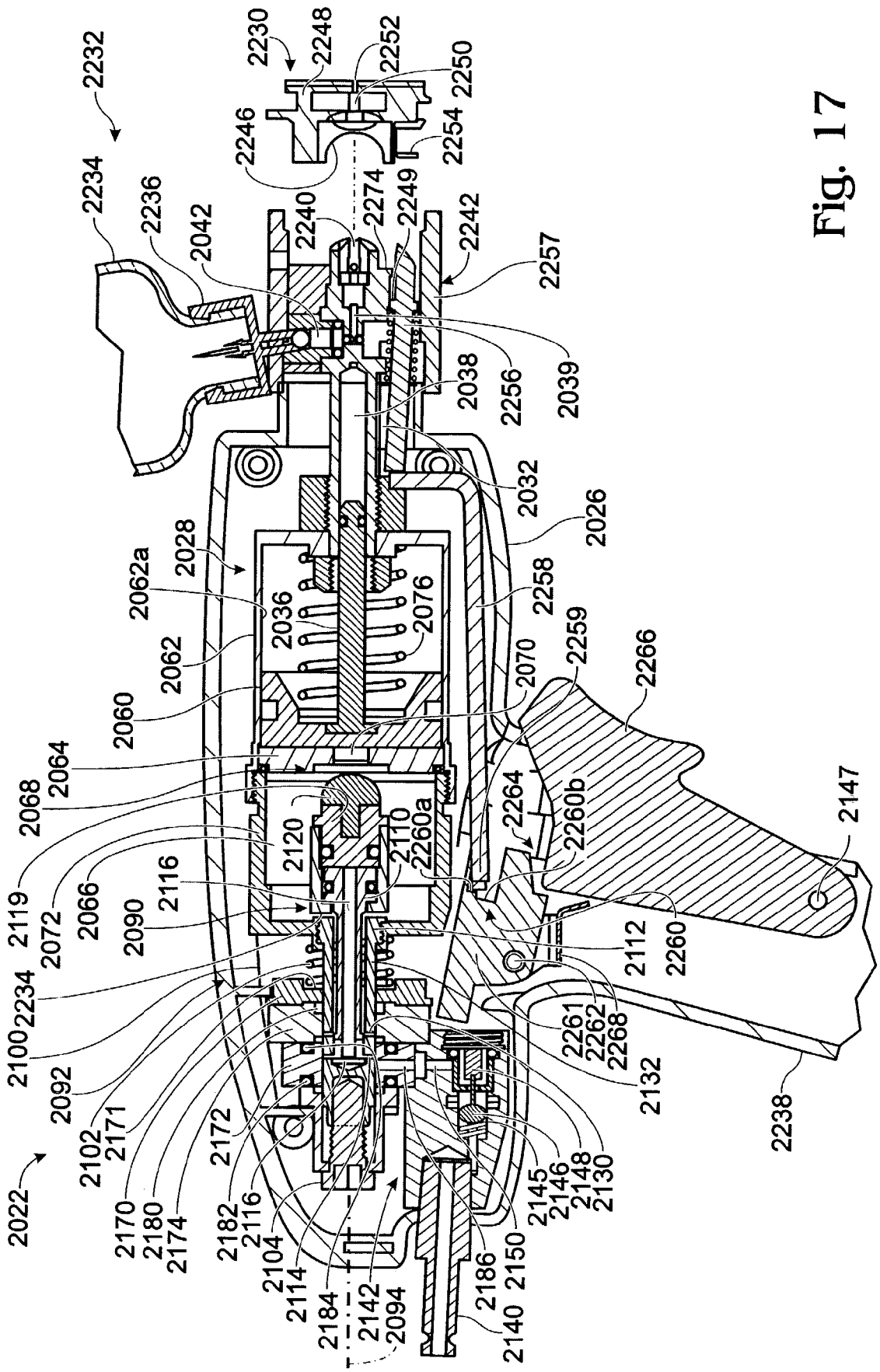
FIG. 17 is a side sectional elevation view of the system of FIG. 16 that depicts the system in a stored position.
Figure 18:
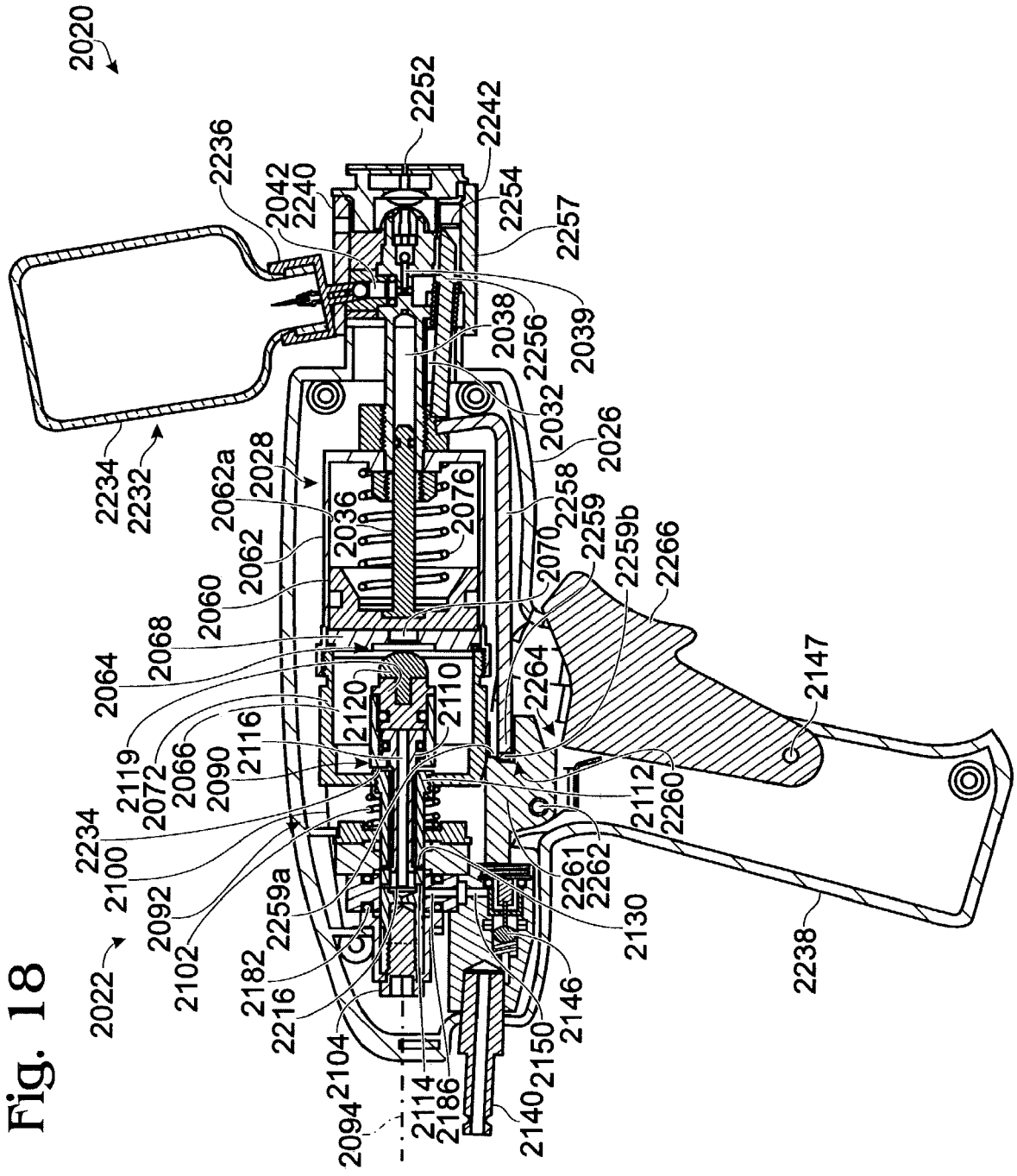
FIG. 18 is a side sectional elevation view of the system of FIG. 16 that depicts the system in an unlocked position.
Figure 19:
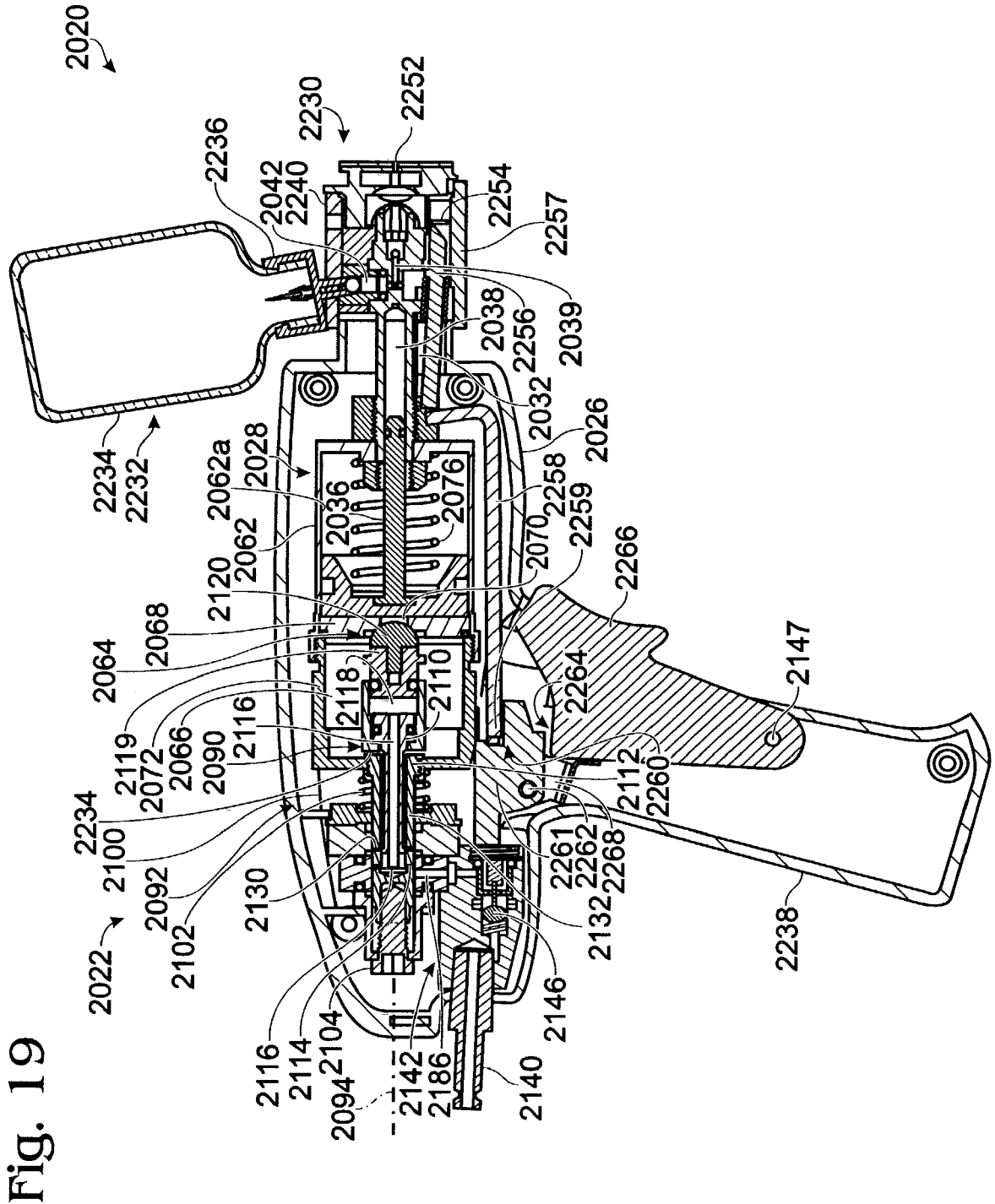
FIG. 19 is a side sectional elevation view of the system of FIG. 16 that depicts the system in a primed position.

FIGS. 16–27 depict a needle-free injection system 2020 according to another embodiment of the invention. Injection system 2020 includes an injection device 2022. FIG. 16 shows injection device 2022 in a first position, which will be referred to as the "disassembled" position. In this position, device 2022 and detachable end assembly 2240 are separated, as for cleaning. FIG. 17 shows the device in the "locked" or "stored" position. In this position, end assembly 2240 is attached to device 2022, but disposable nozzle assembly 2230 is not. Moreover, trigger 2266 is locked and cannot be actuated. FIG. 18 depicts device 2022 in the "unlocked" or "reset" position. In this position, disposable nozzle assembly 2230 is inserted into end assembly 2240 and trigger 2266 is unlocked. FIG. 19 depicts device 2022 in a position which will be referred to as the "primed," or "priming" position. In this position, trigger 2266 has been actuated, but the device has not been fired. FIG. 20 depicts device 2022 in a position which will be referred to as the "fired" or "firing" position.

For the sake of clarity, those elements of the injection device shown in FIGS. 16–28 that perform the same or a similar function as elements of the injection device described with respect to FIGS. 1–3 or 15–19 are given corresponding reference numbers in the two thousands range. For example, where the injection device in FIGS. 1–3 is given the reference number 22, the injection device in FIGS. 11–15 is given the reference number 1022, and the injection device in FIGS. 16–28 is given the reference number 2022. Moreover, it should be appreciated that any of the elements described with respect to the embodiments shown in FIGS. 1–15 may be incorporated into the device shown in FIGS. 16–28 and vice versa.

Initially turning to FIG. 16, as in the embodiments described above, injection device 2022 is configured to inject a dose of a drug or other fluid into a subject. This is accomplished by using pressurized gas to expel fluid from the injection device. The pressurized gas may be supplied from a tank, cartridge or other source, and typically is delivered through device 2022 and vented via operation of various valve structures. System 2020 may include a fluid supply 2232 that may be coupled with injection device 2022 in order to supply the injection device with fluid, such as drugs, vaccines or other injectable fluids. In the depicted embodiment, fluid supply 2232 takes the form of a injectable fluid-filled bottle 2234. Bottle 2234 is connected to device 2022 via a vial adapter 2236. Suitable vial adapters are described in U.S. Pat. Nos. 5,466,220 and 5,893,397, each of which is hereby incorporated by reference in its entirety for all purposes. Vial adapter 2236 may be held in place in injection device 2022 via a friction fit with a conventional seal arrangement.

As shown, injection device 2022 may include an outer housing 2026, which may include a handle 2238 that is adapted to be comfortably held in a user's hand. The depicted housing is formed from injection-molded plastic, though various other materials and fabrication methods may be employed as desired.

Injection device 2022 typically includes a fluid expulsion mechanism, such as syringe assembly 2028, that is configured to draw in and forcibly expel drugs or other fluids. As shown in the figures, syringe assembly 2028 may be disposed at least partially within housing 2026 toward a forward end of the housing.

In some embodiments, syringe assembly 2028 may include a detachable end assembly 2240. Detachable end assembly 2240 may include an end cap 2241 and an attachment end 2242. As shown, end cap 2241 is typically detachably connected to end attachment end 2242 and attachment end 2242 is typically detachably connected to outer housing 2026, thereby allowing a user to periodically disassemble and clean device 2022. End cap 2241 may aid to protect device 2022 during storage.

Turning to FIG. 17, in preparation for use, the end cap may be replaced with a disposable nozzle assembly 2230. Typically, in order to prevent cross-contamination between patients, or for any other reason, a new disposable nozzle assembly 2230 is attached to device 2022 before each injection. FIG. 21 depicts a top cross sectional view of a nozzle assembly 2230 inserted into attachment end 2242. As shown, protuberances 2270 on nozzle assembly 2230 are grasped and secured by detents 2272 on end assembly 2230.

Returning to FIG. 17, disposable nozzle assembly 2230 may include an inner portion 2246 and an outer portion 2248. Inner portion 2246 includes an orifice 2250, which is adapted to align with outlet 2040 when disposable nozzle assembly 2230 is attached to device 2022. Outer portion 2248 includes a discharge outlet 2252 adapted to align with orifice 2250 and outlet 2040, creating a discharge pathway that includes outlet 2040, orifice 2250 and discharge outlet 2252. Discharge outlet 2252 is typically of substantially greater size than orifice 2250 so that the flow of fluid from the orifice is not restricted by the discharge outlet.

As shown in FIGS. 26–30, a penetrable membrane or web 2244 may be located along the discharge pathway. Use of a penetrable membrane may, for example, prevent splashback from contaminating the non-disposable portions of device 2022. In this respect, the membrane acts as a check valve. Membrane 2244 is typically made of a material that can be penetrated by a liquid stream traveling with the force typically produced by a device like device 2022. For example, membrane 2244 may be made of medical grade rubber such as silicon, chlorobutyl, bromobutyl, ethylene propylene, or a fluoroelastomer such as that sold under the trademark Viton® by DuPont Dow Elastomers, LLC (Wilmington, Del.).

Figure 28:
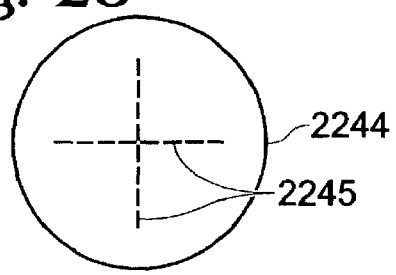
FIG. 28 is a schematic illustration of a penetrable membrane suitable for use with the present invention.

It may be desirable to include score-lines 2245 on the membrane to ease penetration by a fluid stream, as shown in FIG. 28. It will be appreciated that the length, pattern and number of score-lines shown in FIG. 28 is exemplary and that any suitable length, pattern, or number of score-lines may be used, or they may be deleted altogether.

Membrane 2244 may be any desirable thickness, but in a preferred embodiment, membrane 2244 is from between 0.004–0.008 inches (0.1–0.2 mm) in thickness. Of course it will be appreciated that the suitable thickness will be dependent upon a number of factors including the material used, the force produced by the device, and whether or not the membrane is pre-scored.

Figure 26:
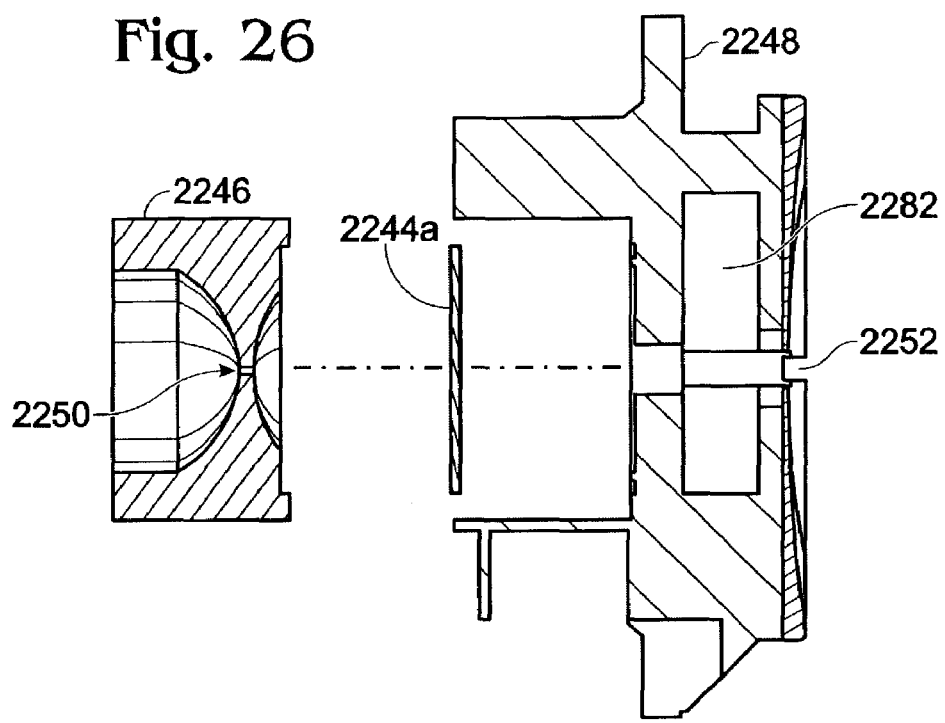
FIG. 26 is a schematic partial side sectional view of the system of FIG. 16 including a first embodiment of a penetrable membrane.

In a preferred embodiment, as shown in FIG. 26, a penetrable membrane 2244a is sandwiched between inner portion 2246 and outer portion 2248, such that fluid traveling along the discharge pathway must travel through, i.e. penetrate, membrane 2244a, before exiting device 2022. As shown, area 2282 may be left open to act as a splash-back aeration area. Membrane 2244a may be of any desirable shape, suitable for use in device 2022. For example, membrane 2244a may take the form of an insertable disk.

Figure 27:
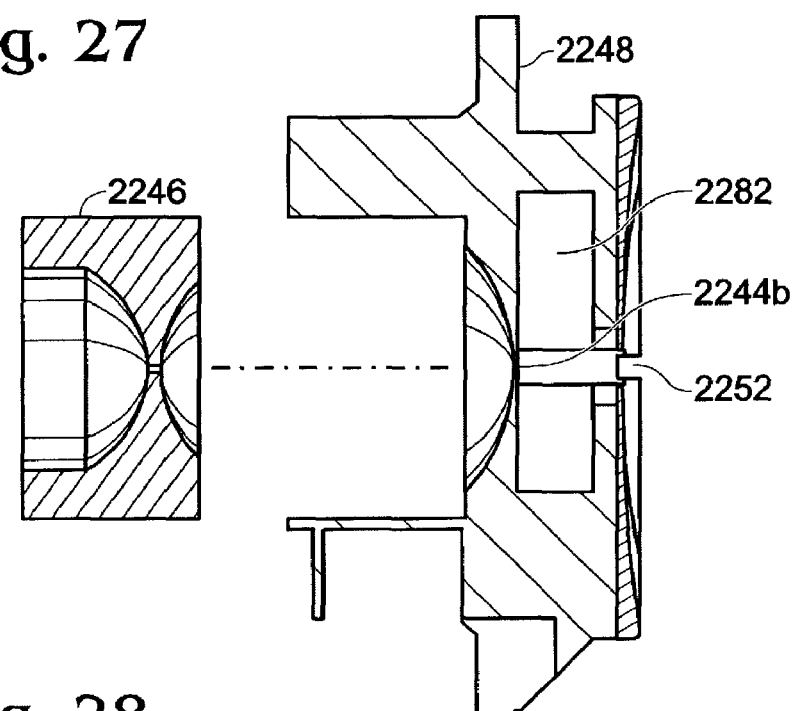
FIG. 27 is a schematic partial side sectional view of the system of FIG. 16 including a second embodiment of a penetrable membrane.

An alternate embodiment is shown in FIG. 27. In this embodiment, rather than including a discharge outlet 2252, the area of outer portion 2248 that aligns with outlet 2040 and orifice 2250 is extremely thin, creating a penetrable membrane 2244b.

Figure 29:
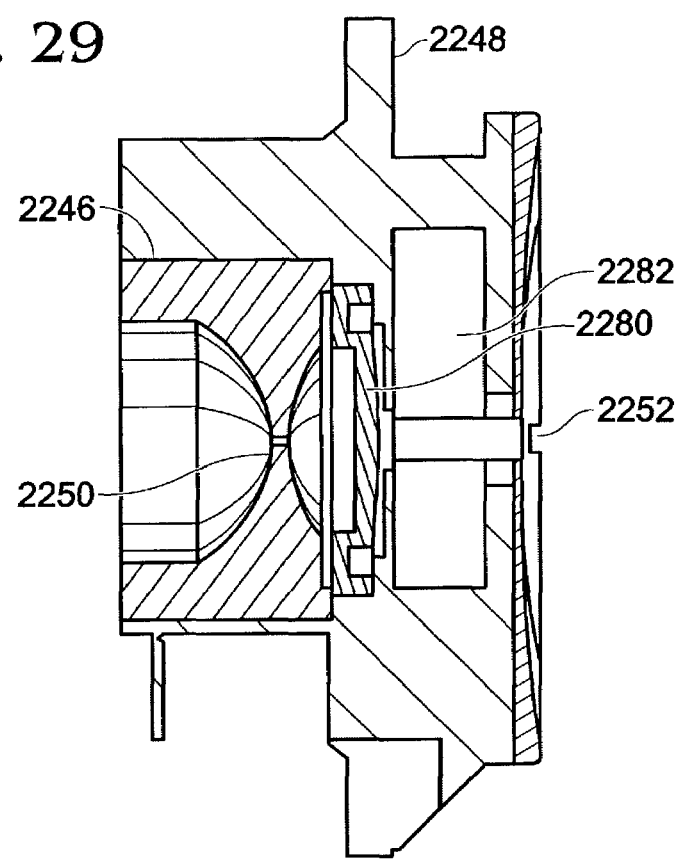
FIG. 29 is a schematic partial side sectional view of the system of FIG. 16 including a third embodiment of a penetrable membrane.
Figure 30:
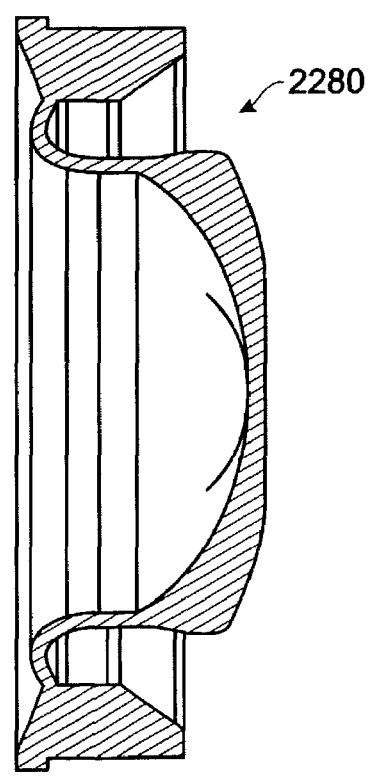
FIG. 30 is a schematic illustration of a penetrable membrane suitable for use with the system shown in FIG. 29.

In a more preferred embodiment, as shown in FIG. 29, disposable nozzle assembly 2230 may include a valve member 2280 sandwiched between inner portion 2246 and outer portion 2248. Typically, valve member 2280 is configured to allow only uni-directional fluid flow. For example, valve member 2280 may allow fluid to flow out of device 2022 and at the same time, prevent reentrance of any fluid backflow or splashback from the injection site into the device. FIG. 30 shows a close-up cross-sectional view of a suitable valve member 2280 showing the radial curvature of the valve. Valves are well known to those of skill in the art. A suitable commercially available valve is the MediFlo®-SureFlo® Valve sold by Liquid Molding Systems (Midland, Mich.).

Returning to FIG. 17, nozzle assembly 2230 includes a frangible tab 2254, which is configured to align with a penetrating member 2256. Penetrating member 2256 is outwardly biased (toward the right, as depicted) by spring 2257, which in the storage position shown in FIG. 17, urges nubs 2274 on penetrating member 2256 against lip 2249 on end assembly 2242. Penetrating member 2256 abuts L-shaped locking pin 2258, the distal end 2259 of which is received by a recessed portion 2260 of trigger lock 2261. As shown, recessed portion 2260 may include two or more positioning regions, 2260a and 2260b, in which distal end 2259 may be seated.

Trigger lock 2261 is configured to pivot about point 2262 and includes a recessed portion 2264, which, when trigger lock 2661 is in the correct orientation, is adapted to receive a portion of trigger 2266 and prevent actuation thereof. Cylinder lock 2268, a portion of which is configured to abut trigger 2266, is likewise pivotally connected to point 2262.

A plunger 2036 is slidably disposed within fluid cylinder 2032, thereby defining a variable-volume fluid reservoir 2038. When plunger 2036 is advanced (i.e., moved to the right, as depicted), fluid is expelled out of fluid reservoir 2038 via fluid path 2039, through an outlet 2040, and out of discharge outlet 2252 in nozzle assembly 2230. Retraction of plunger 2036 (i.e., moving the plunger to the left, as depicted) draws fluid from fluid supply 2232 into fluid reservoir 2038 through inlet 2042.

In the depicted syringe assembly, outlet 2040 and inlet 2042 typically are provided with check valves to prevent backflow. Various types of valves may be used, including ball-type check valves.

As indicated, a piston 2060 may be secured to plunger 2036. In the depicted embodiment, piston 2060 is slidably disposed within a piston cylinder 2062, and creates a substantially sealed interface with an interior wall 2062a of the piston cylinder. As will be explained in more detail below, when a poppet valve 2064 opens (shown in FIG. 20), pressurized gas from a gas reservoir 2066 is allowed to escape past a gas bulkhead 2068 through a bulkhead opening 2070. Gas reservoir 2066 is contained within a gas cylinder 2072, which is fixedly secured relative to bulkhead 2068 and piston cylinder 2062. Upon the opening of poppet valve 2064, the pressurized gas exerts upon operative surface 2060a of piston 2060, causing piston 2060 and plunger 2036 to advance forward and expel fluid from syringe assembly 2028 through nozzle assembly 2230, as described above. The area between bulkhead 2068 and piston 2060 created by the advancement of piston 2060 will be referred to as piston chamber 2074 (FIG. 20). As indicated, a return spring 2016 may be provided to urge piston 2060 back toward bulkhead 2068 upon venting of pressurized gas within piston chamber 2074 and gas reservoir 2066.

As indicated above, piston cylinder 2062 typically is fixedly secured to gas bulkhead 2068 and gas cylinder 2072. Toward the rear half of housing 2026, a slidable valve structure 2090 is fixedly secured to gas cylinder 2072. Piston cylinder 2062, gas cylinder 2072 and slidable valve structure 2090 collectively form a reciprocating structure 2092 which moves back and forth relative to housing 2026 along axis 2094. Syringe assembly 2028 is secured to the forward end of reciprocating structure 2092, and thus also moves relative to housing 2026. Toward the rear of reciprocating structure 2092, slidable valve structure 2090 is slidably supported within a valve body 2100 that is fixedly secured within housing 2026.

During operation, reciprocating structure 2092 is progressively pushed into housing 2026 from the position shown in FIG. 18, to the position shown in FIG. 20. Normally, this occurs as a result of pressing the end of nozzle assembly 2230 against an injection site while manually gripping handle 2238. Spring 2102 is compressed as reciprocating structure 2092 moves in a rearward direction relative to housing 2026. Upon removal of the compressing force, spring 2102 urges reciprocating structure 2092 back toward the position shown in FIG. 18.

Returning to FIG. 17, slidable valve structure 2090 may include an inner valve sleeve 2110 and an outer valve sleeve 2112. In the depicted exemplary embodiment, outer valve sleeve 2112 includes a first set of holes 2114 which fluidly communicate with a bore passage 2116 defined through the center of inner valve sleeve 2110. Bore passage 2116 fluidly couples with a poppet reservoir 2118 (FIG. 19) defined in part by poppet seat 2119. Poppet seat 2119 is adapted to retain a poppet 2120. In the depicted embodiment, poppet seat 2119 is slidably movable back and forth on the end of slidable valve structure 2090. When poppet seat 2119 is in its forward-most position, as shown in FIG. 18, poppet 2120 seats into a valve seat in bulkhead 2068, thus sealing off gas reservoir 2066 from piston chamber 2074 (FIG. 20). Fore-and-aft movement of poppet seat 2119 typically is controlled by gas pressure existing in poppet reservoir 2118 and gas reservoir 2066.

Outer valve sleeve 2112 may include another set of holes 2130, which fluidly communicate with a cylindrical passage 2132. As indicated, passage 2132 may be defined between the inner and outer valve sleeves. Cylindrical passage 2132 fluidly couples with gas reservoir 2066 via holes 2134.

As shown in FIG. 17, a gas fitting 2140 may be provided into housing 2026, to enable the injection device to be supplied with compressed air or some other pressurized gas via a gas hose (not shown). The delivery of pressurized gas through the device typically is controlled via a supply valve assembly 2142, which is actuated by inserting an unused nozzle 2230 into device 2022. As shown, supply valve assembly 2142 may include a valve 2146 biased into a closed position by a spring 2145, a supply valve plunger 2148 secured to supply valve 2146, and a supply conduit 2150 through which pressurized gas is provided upon opening of the valve.

As will be described in greater detail below, insertion of an unused nozzle 2230 into device 2022 results in a slight counter clockwise rotation of trigger lock 2261. This movement of trigger lock 2261 causes valve plunger 2148 to move inward. Inward movement of valve plunger 2148 moves supply valve 2146 inward into an open position, allowing pressurized gas to pass beyond supply valve 2146 and be delivered to other parts of device 2022 via a supply conduit 2150.

Valve body 2100 includes a forward section 2170, a rear section 2172, and an intermediate section 2174. A spring 2102 extends between and urges against a recessed region 2171 of forward section 2170 and the rear end of gas cylinder 2072. Three U-cup seals 2180, 2182 and 2184 are provided between the pieces of the valve body. The area of rear section 2172 between seals 2182 and 2184 provides a supply chamber 2186 that is fluidly coupled with supply conduit 2150 of supply valve assembly 2142.

Accordingly, it Will be appreciated that moving slidable valve structure 2090 backward and forward relative to valve body 2100 (e.g., by pushing reciprocating structure 2092 into housing 2026) controls pressurization and venting of the various passages in slidable valve structure 2090. Referring to FIG. 20, for example, valve structure 2090 is positioned so that holes 2114 in outer valve sleeve 2112 are aligned slightly to the rear of seal 2184, allowing bore passage 2116 and poppet reservoir 2118 to vent to atmosphere. In FIG. 18, holes 2130 are aligned slightly to the front of seal 2182, allowing cylindrical passage 2132 and gas reservoir 2066 to vent to atmosphere. In FIGS. 18–20, holes 2114 and/or holes 2130 are at times aligned with supply chamber 2186, such that the respective passages and reservoirs are equalized in pressure relative to the supply chamber. Accordingly, in such a state of alignment, opening supply valve 2146 would pressurize the respective passages/reservoirs.

Operation of the Depicted Injection Devices

The operation of injection device 2022 will now be described with reference to FIGS. 16–20 and 22–25. Operation of devices 22 and 1022 is described in copending U.S. Pat. No. 6,676,630, filed Jun. 2, 2002 which is hereby incorporated by reference for all purposes.

Figure 22:
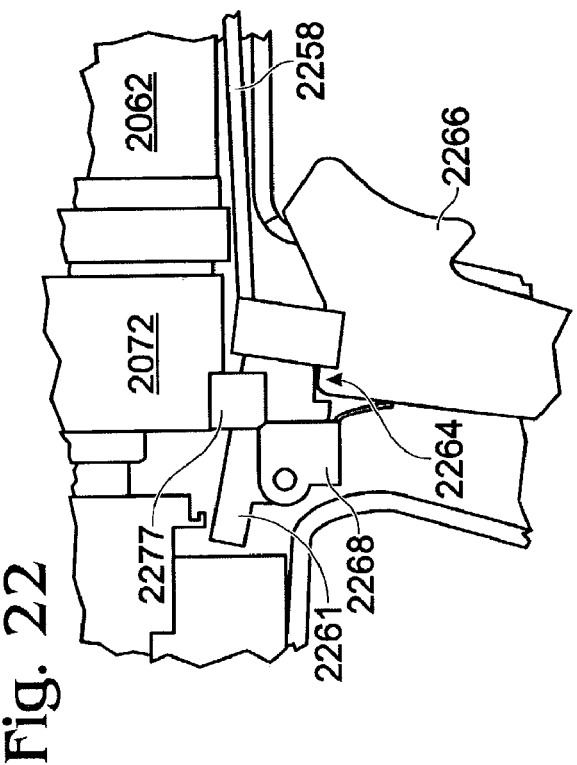
FIG. 22 is a partial side elevation view of the system of FIG. 16 that depicts the system in a stored position.
Figure 24:
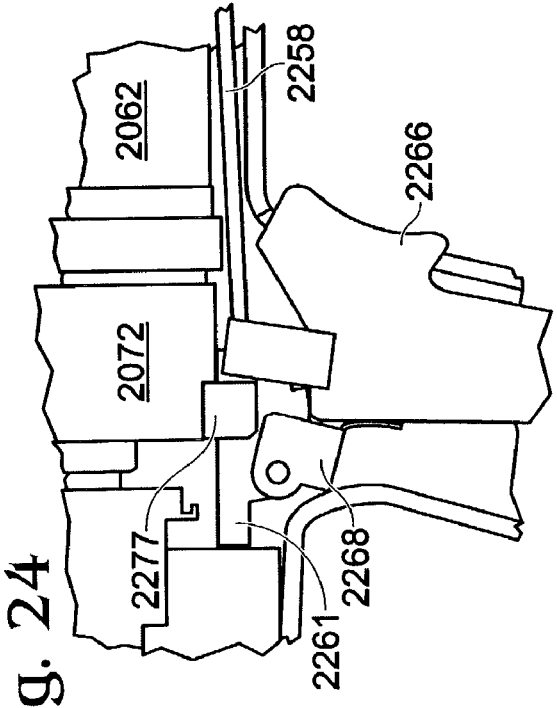
FIG. 24 is a partial side elevation view of the system of FIG. 16 that depicts the system in a primed position.

When device 2022 is in the stored position, device 2022 is in the position shown in FIG. 18. Specifically, detachable end assembly 2240 may be attached to device 2022, but a unused disposable nozzle assembly has not yet been installed. In this position, trigger 2266 is locked and cannot be actuated. FIG. 22 is a partial side view of device 2022 in the stored position. As shown; the upper right hand corner of trigger 2266 is seated within recessed portion 2264 of trigger lock 2261 and immobilized thereby.

Viewing FIGS. 17, 18, 22, and 23, trigger 2266 is unlocked by inserting a new, unused, nozzle assembly 2230 in end 2242. As nozzle assembly 2230 is inserted into end 2242, frangible tab 2254 of nozzle assembly urges penetrating member 2256 rearward (or towards the left, as depicted) against the bias of spring 2257. Rearward movement of penetrating member 2256 pivots L-shaped locking pin 2258 enough to move the distal end of L-shaped locking pin 2258 from positioning region 2259a to 2259b. Movement of L-shaped locking pin 2258 forces trigger lock 2261 to pivot counterclockwise about axis 2262, moving recessed portion 2264 upwards and thereby release trigger 2266 for movement. As shown in FIG. 22, movement of trigger lock 2261 also positions cylinder lock 2268 against u-shaped piston cylinder projection 2277, thereby blocking rearward movement of gas cylinder 2072 and piston cylinder 2062.

As described above, movement of trigger lock 2261 also opens supply valve 2146, which allows pressurized gas to flow through supply conduit 2150 into supply chamber 2186. In the position shown in FIG. 18, holes 2114 are aligned with supply chamber 2186. Bore passage 2116 is thus pressurized by the opening of supply valve 2146, which causes poppet 2120 to move forward and close the poppet valve, sealing off bulkhead 2068 between gas reservoir 2066 and piston chamber 2074.

Figure 23:
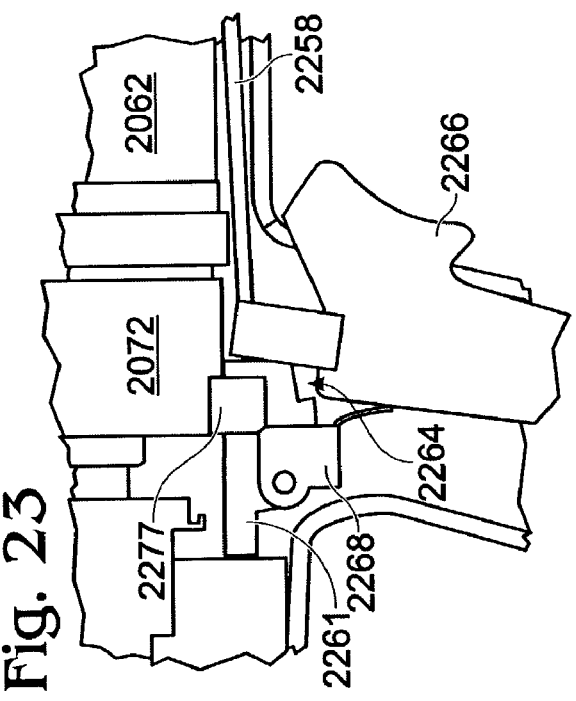
FIG. 23 is a partial side elevation view of the system of FIG. 16 that depicts the system in an unlocked position.
Figure 25:
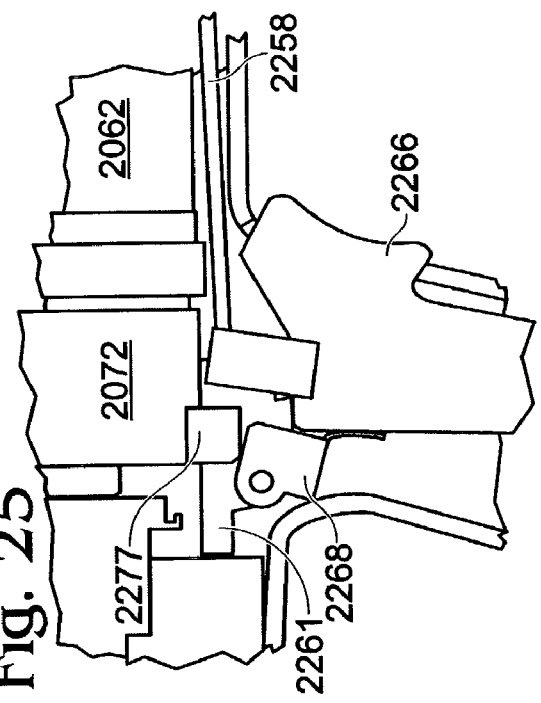
FIG. 25 is a partial side elevation view of the system of FIG. 16 that depicts the system in a fired position.

Once trigger 2266 is unlocked, the operator is able to press trigger 2266 inward. As shown in FIG. 23, depressing trigger 2266 rotates cylinder lock 2268 clockwise about pivot point 2262, releasing projection 2277 and piston cylinder 2062. Depressing trigger 2266 also causes reciprocating structure 2092 to be pushed somewhat into housing 2026, moving device 2022 from the position shown in FIG. 18 to the position shown in FIG. 19. In FIG. 19, holes 2114 are still aligned with supply chamber 2186, but the slidable valve assembly has moved far enough rearward so that holes 2130 are now also aligned with supply chamber 2186. Thus, gas reservoir 2066 is pressurized (charged) via holes 2130 and cylindrical passage 2132. Poppet reservoir 2118 remains pressurized in FIG. 19, such that poppet valve 2064 is held closed and no gas escapes into piston chamber 2074. Plunger 2036 thus remains in its fully withdrawn position.

As the operator pushes nozzle assembly 2230 against the injection site, reciprocating structure 2092 is pushed further into housing 2026. At some point, slidable valve structure 2020 slides far enough rearward so that holes 2214 pass beyond U-cup seal 2284, as seen in FIG. 20. When holes 2114 pass beyond seal 2184, poppet reservoir 2118 is allowed to vent to atmosphere through bore passage 2116. At this point, there is a high pressure differential between gas reservoir 2066 and atmosphere (e.g., 800 p.s.i. or greater), which causes poppet 2120 to move rapidly away from bulkhead 2068 and into its rearmost position.

This opens poppet valve 2064, which causes the pressurized gas that was contained within gas reservoir 2066 to act upon operative surface 2060a of piston 2060, causing injectable fluid to be rapidly expelled from fluid reservoir 2038, travel through fluid path 2039, and exit the device through discharge outlet 2252.

When trigger 2266 is released by the user, it returns to the locked position shown in FIG. 22. However, rearward movement of piston cylinder 2062 when device 2022 is fired, forces penetrating member 2256 against frangible tab 2254 with sufficient force to break the tab, rendering the current disposable nozzle 2230 if reinserted into the device 22 incapable of urging penetrating member 2256 rearwards in order to release trigger 2266 from the locked position. This ensures that each disposable nozzle is used only once.

FIG. 20 shows piston 2060 in its fully advanced position, and reciprocating structure 2092 in its rearmost position relative to housing 2026. At this point, gas reservoir 2066 and piston chamber 2074 have not yet vented, and those areas remain at a substantial pressure differential above atmosphere. Piston 2060 thus remains advanced. As housing 2026 is withdrawn from the injection site, spring 2102 urges reciprocating structure 2092 forward relative to housing 2026. This in turn causes slidable valve structure 2090 to move relative to valve body 2100. Eventually, gas reservoir 2066 and piston chamber 2074 are vented when holes 2130 of valve structure 2090 pass forward beyond U-cup seal 2180. As the pressure is released, spring 2076 urges against piston 2060, causing it to return from its advanced position to its retracted position against bulkhead 2068, as seen in FIG. 18.

As piston 2060 retracts, plunger 2036 is retracted from its advanced position within fluid reservoir 2038. The retreat of plunger 2036 opens inlet check valve 2052 and draws a new dose of fluid into fluid reservoir 2038. The outlet check valve remains closed, due to its spring and the vacuum pressure created by the retraction of plunger 2036. Eventually, the device returns to the primed position shown in FIG. 18 and is ready to deliver another injection of fluid in the manner just described.

While the present invention has been particularly shown and described with reference to the foregoing preferred embodiments, those skilled in the art will understand that many variations may be made therein without departing from the spirit and scope of the invention as defined in the following claims. The description of the invention should be understood to include all novel and non-obvious combinations of elements described herein, and claims may be presented in this or a later application to any novel and non-obvious combination of these elements. Where the claims recite "a" or "a first" element or the equivalent thereof, such claims should be understood to include incorporation of one or more such elements, neither requiring nor excluding two or more such elements.

We claim:

1. A needle-free injection device, comprising:
    a syringe assembly configured to draw in and expel injectable fluid; and
    a locking mechanism configured to prevent actuation of the device;
    a disposable nozzle configured to temporarily engage the housing and including a deactivatable mechanism for temporarily unlocking the locking mechanism, the disposable nozzle being in fluid communication with the syringe assembly when the disposable nozzle is engaged with the housing;
    wherein upon firing of the device, the mechanism for temporarily unlocking the locking mechanism is permanently deactivated.

2. The needle-free injection device of claim 1, further comprising:
    a power delivery assembly configured to deliver an operative force to the syringe assembly, thereby causing the syringe assembly to expel injectable fluid.

3. The needle-free injection device of claim 2, wherein pushing the nozzle assembly against an injection site causes the syringe assembly and power delivery assembly to move relative to each other and such movement causes the power delivery assembly to deliver the operative force to the syringe assembly.

4. The needle-free injection device of claim 3, wherein the locking mechanism is configured to prevent movement of the power delivery assembly and syringe assembly relative to each other.

5. The needle-free injection device of claim 4, wherein the locking mechanism includes a rotatable trigger lock pivotably fixed to the housing, the rotatable trigger lock being configured, in a first position, to position an actuation-prevention portion so as to prevent movement of the power delivery assembly and the syringe assembly relative to each other.

6. The needle-free injection device of claim 5, further comprising:
a trigger configured to, upon actuation, deactivate the locking mechanism; and
a trigger lock configured to prevent actuation of the trigger, the trigger lock comprising:
a slidable piercing member; and
a locking pin configured to move from a first position to a position upon engagement with the slidable piercing member; wherein,
when the locking pin is in the first position, the locking mechanism is locked and the trigger is blocked from actuation, and
when the locking pin is in the second position, the locking mechanism is unlocked and the trigger can be actuated.

7. The needle-free injection device of claim 6, wherein the trigger is blocked from actuation by the rotatable trigger lock and movement of the locking pin from the first lock position to the second position rotates the rotatable member, freeing the trigger.

8. The needle-free injection device of claim 2, further comprising a trigger configured, upon actuation, to deactivate the locking mechanism.

9. The needle-free injection device of claim 8, wherein the locking mechanism further includes a trigger lock, the trigger lock being configured to prevent actuation of the trigger.

10. The needle-free injection device of claim 9, wherein: the trigger lock includes:
a slidable piercing member; and
a locking pin configured to move from a first position to a second position upon engagement with the slidable piercing member; wherein,
when the locking pin is in the first position, the locking mechanism is locked and the trigger is blocked from actuation, and
when the locking pin is in the second position, the locking mechanism is unlocked and the trigger can be actuated.

11. The needle-free injection device of claim 10, wherein the trigger is blocked from actuation by a rotatable trigger lock and movement of the locking pin from the first position to the second position rotates the rotatable member, freeing the trigger.

12. The needle-free injection device of claim 1, wherein the disposable nozzle includes a frangible tab adapted to engage the slidable piercing member when the disposable nozzle is engaged with the housing.

13. The needle-free injection device of claim 12, wherein when the frangible tab engages the slidable piercing member, the locking pin is moved from the first position to the second position.

14. The needle-free injection device of claim 13, wherein upon firing of the device, the slidable piercing member pierces and breaks the frangible tab.

15. The needle-free injection device of claim 1, wherein the syringe assembly is configured to expel injectable fluid upon application of pressurized gas to the syringe assembly from a gas reservoir.

16. The needle-free injection device of claim 15, further comprising a trigger lock configured to prevent delivery of pressurized gas to the syringe assembly.

17. The needle-free injection device of claim 16, wherein pushing the nozzle assembly against an injection site causes the gas reservoir to move relative to the syringe assembly;
movement of the gas reservoir relative to the syringe assembly delivers pressurized gas from the gas reservoir to the syringe assembly; and
the trigger lock is configured to prevent movement of the gas reservoir relative to the syringe assembly.

18. The needle-free injection device of claim 17, wherein the trigger lock is pivotably fixed to the housing, the trigger lock being configured, in a first position, to position an actuation-prevention portion so as to prevent movement of the gas reservoir relative to the syringe assembly.

19. The needle-free injection device of claim 18, further comprising:
a trigger configured to, upon actuation, deactivate the trigger lock, the trigger lock comprising:
a slidable piercing member; and
a locking pin configured to move from a first position to a position upon engagement with the slidable piercing member; wherein,
when the locking pin is in the first position, the locking mechanism is locked and the trigger is blocked from actuation, and
when the locking pin is in the second position, the locking mechanism is unlocked and the trigger can be actuated.

20. The needle-free injection device of claim 19, wherein the trigger is blocked from actuation by the rotatable trigger lock and movement of the locking pin from the first lock position to the second position rotates the rotatable member, freeing the trigger.

21. The needle-free injection device of claim 20, wherein:
pressurized gas is delivered to the gas delivery assembly from a gas supply via a supply valve; and
rotation of the rotatable trigger lock opens the supply valve.

22. A needle-free injection device comprising:
a syringe assembly configured to expel injectable fluid upon application of an operative force to the syringe assembly;
a first delivery mechanism adapted to delivery energy from an external energy supply to an energy reserve;
a second delivery mechanism adapted to deliver the operative force from the energy reserve to the syringe assembly;
a locking mechanism configured to prevent operation of the second delivery mechanism;
a disposable nozzle configured to temporarily fluidly communicate with the syringe assembly, wherein engagement of the disposable nozzle with the syringe assembly initiates operation of the first delivery mechanism and releases the locking mechanism, and wherein the disposable nozzle includes a deactivatable mechanism for initiating operation of the first delivery mechanism and releasing the locking mechanism.

23. The needle-free injection device of claim 22, wherein the deactivatable mechanism is permanently deactivated during or after an injection.

* * * * *